United States Patent [19]

Pearce

[11] Patent Number: 5,393,776
[45] Date of Patent: Feb. 28, 1995

[54] TOCOTRIENOL ANALOGS IN THE TREATMENT OF HYPERCHOLESTEROLEMIA AND HYPERLIPIDEMIA

[75] Inventor: Bradley C. Pearce, East Hampton, Conn.

[73] Assignee: Bristol-Myers Squibb Company, New York, N.Y.

[21] Appl. No.: 242,213

[22] Filed: May 13, 1994

Related U.S. Application Data

[63] Continuation of Ser. No. 890,414, May 29, 1992, abandoned, which is a continuation-in-part of Ser. No. 583,618, Sep. 14, 1990, abandoned.

[51] Int. Cl.⁶ ............... A61K 31/015; A61K 31/035; A61K 31/045; A61K 31/05; A61K 31/055; A61K 31/085; A61K 31/10; A61K 31/12; A61K 31/135; A61K 31/165; A61K 31/18; A61K 31/27; A61K 31/63; A61K 31/69

[52] U.S. Cl. ..................... 514/486; 514/64; 514/485; 514/605; 514/616; 514/617; 514/618; 514/619; 514/621; 514/622; 514/629; 514/646; 514/676; 514/688; 514/689; 514/708; 514/710; 514/713; 514/716; 514/717; 514/720; 514/727; 514/728; 514/730; 514/751; 514/764; 514/824; 560/24; 560/29; 560/30; 564/8; 564/99; 564/155; 564/157; 564/158; 564/161; 564/162; 564/163; 564/167; 564/169; 564/170; 564/175; 564/176; 564/177; 564/183; 564/218; 564/223; 564/305; 564/440; 564/442; 564/443; 568/1; 568/2; 568/6; 568/27; 568/28; 568/30; 568/31; 568/32; 568/33; 568/35; 568/36; 568/37; 568/38; 568/39; 568/42; 568/43; 568/44; 568/45; 568/46; 568/51; 568/54; 568/55; 568/56; 568/306; 568/335; 568/336; 568/337; 568/584; 568/587; 568/588; 568/630; 568/648; 568/649; 568/650; 568/651; 568/654; 568/656; 568/657; 568/662; 568/663; 568/705; 568/706; 568/709; 568/715; 568/716; 568/764; 568/765; 568/766; 568/774; 568/780; 568/811; 568/812; 568/813; 570/128; 570/182; 585/24

[58] Field of Search ................. 514/64, 485, 486, 605, 514/616, 617, 618, 619, 621, 622, 629, 646, 676, 688, 689, 708, 710, 713, 716, 717, 720, 727, 728, 730, 751, 764, 824; A61K 31/015, 31/035, 31/045, 31/05, 31/055, 31/085, 31/10, 31/12, 31/135, 31/165, 31/18, 31/27, 31/63, 31/69

[56] References Cited

U.S. PATENT DOCUMENTS

| | | | |
|---|---|---|---|
| 4,080,474 | 3/1978 | Hindley et al. | 514/689 |
| 4,603,142 | 7/1986 | Burger et al. | 514/456 |
| 4,992,469 | 2/1991 | Ozawa et al. | 514/559 |
| 5,217,992 | 6/1993 | Wright et al. | 514/458 |
| 5,321,046 | 6/1994 | Sit et al. | 514/522 |

Primary Examiner—Glennon H. Hollrah
Assistant Examiner—Scott C. Rand
Attorney, Agent, or Firm—Frank P. Hoffman

[57] ABSTRACT

This invention relates to structurally novel acyclic tocotrienol analogs, which are useful for cholesterol/lipid lowering in cases of hypercholesterolemia and hyperlipidemia, and for atherosclerosis. Also provided are pharmaceutical compositions and a method of use employing those compositions.

29 Claims, No Drawings

TOCOTRIENOL ANALOGS IN THE TREATMENT OF HYPERCHOLESTEROLEMIA AND HYPERLIPIDEMIA

BACKGROUND OF THE INVENTION

1. Field of the Invention

This application is a continuation of Ser. No. 07/890,414, filed May 29, 1992, now abandoned, which is a continuation-in-part of Ser. No. 07/583,618, filed on Sep. 14, 1990, now abandoned.

The present invention relates to structurally novel acyclic tocotrienol analogs, which are useful for cholesterol/lipid lowering in cases of hypercholesterolemia and hyperlipidemia, and for atherosclerosis. Also provided are pharmaceutical compositions and a method of use employing those compositions.

2. Description of the Prior Art

It is generally recognized that high blood cholesterol levels are a significant risk factors in cardiovascular disease. Studies have demonstrated that with very few exceptions, populations which consume large quantities of saturated fat and cholesterol have relatively high concentrations of serum cholesterol and high mortality rate from coronary heart disease.

It has been established that 3-hydroxy-3-methylglutaryl coenzyme A reductase (HMGR) is the rate limiting enzyme in the biosynthetic pathway for cholesterol, that inhibition of HMGR activity results in a decrease in serum total cholesterol and LDL cholesterol levels, and that a decrease in serum LDL-cholesterol levels is reflected in a reduction of plasma level of apolipoprotein B. (Brown, et al, *J. Lipid Res,* 21: 505–517 (1980)).

Tocotrienols have been shown to suppress HMGR resulting in the inhibition of cholesterol biosynthesis and a subsequent drop in LDL cholesterol, apolipoprotein B, thromboxane $B_2$, platelet factor 4 and glucose levels. Wright, et al, *A Symposium On Drugs Affecting Lipid Metabolism,* Houston, Tex. (November, 1989). In *J. Biol. Chem,* 261: 10544–10550, (1986), Qureshi, et al. indicated that the hypocholesterolemic effects of alpha-tocotrienol is brought about by the suppression of HMGR as measured by hepatic HMGR activity. Wright et al, supra, showed that tocotrienol-rich fraction (TRF) fed to hypercholesterolemic swine resulted in a dramatic decrease in serum total cholesterol and LDL-cholesterol levels. Qureshi, et al, in *Suppression of Cholesterolgenesis in Hypercholesterolemic Humans by Tocotrienols of Barley and Palm Oils,* presented at the Antioxidant and Degenerative Diseases Conference, Berkeley, Calif., (January, 1990), showed that gamma and delta-tocotrienols suppress HMGR activity. U.S. Pat. No. 4,603,142 to Qureshi et al., (1986) discloses the use of alpha-tocotrienol for the lowering of lipids.

The tocotrienols are structurally related to the tocopherols (vitamin E) and differ only by possessing unsaturation in the isoprenoid side chain. Like the tocopherols, the tocotrienols have antioxidative activity, (Yamaoka, et al, Yukagaku, 34: 120–122 (1985)). Active oxygen species are known to play pivotal roles in the genesis of atherosclerotic plaques, thrombotic episodes, ischemic damage, cancer, aging, dementia, and inflammatory conditions. Of particular interests are the potential protective effects of antioxidants on lipoproteins, since oxidized LDL is thought to be atherogenic. The antioxidative activity of the tocotrienols may be of value in conjunction with their hypolipidemic properties.

Our objective was to find a chemically simplified and more potent class of novel hypolipidemic/antioxidant compounds, possessing a tocotrienol-type profile. A modification was found in which the benzopyran ring of tocotrienols was opened, leading to acyclic tocotrienol analogs. The acyclic tocotrienol analogs were found to exhibit similar cholesterol suppressive activity to that of the tocotrienols.

The present invention describes the synthesis and preliminary biological evaluation of acyclic tocotrienol analogs. The acyclic tocotrienol analogs are chemically simpler than the tocotrienols, having no chiral centers, and can be prepared in few steps from inexpensive starting materials.

SUMMARY OF THE INVENTION

The present invention provides analogs of tocotrienol of the Formula (I)

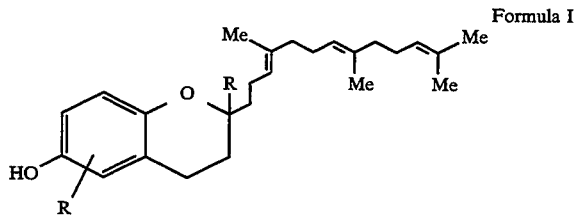

Formula I wherein R represents hydrogen or methyl.

In particular, the present invention provides acyclic tocotrienol analogs which have the general structural Formula II (below) and prodrugs of the compounds of Formula II which prodrugs have the general structural Formula III (below).

Also included within the scope of the present invention are the pharmaceutically acceptable acid addition salts, the metal salts and the solvates of the compounds of Formulas II and III which may exist in various tautomeric forms.

In another aspect, the present invention provides a pharmaceutical composition which comprises at least one compound of Formula II or III and a non-toxic pharmaceutically acceptable carrier or diluent.

In yet another embodiment, the present invention provides a method of treating hypercholesteremia, hyperlipidemia and thromboembolic disorders which consists of administering at least one compound of Formulas II or III to a bird or mammal in need of such treatment.

DETAILED DESCRIPTION OF THE INVENTION

The compounds of the present invention are structurally novel compounds that suppress HMGR, resulting in lowering serum total cholesterol and LDL-cholesterol levels in birds and mammals.

The present invention provides acyclic tocotrienol analogs which have the general structural Formula (II)

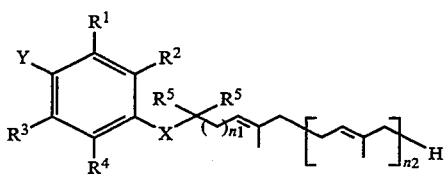

wherein $R^1$, $R^2$, $R^3$, and $R^4$ represent hydrogen, $C_1$–$C_5$ lower alkyl, halogen, $COCH_3$, $CH_2OH$, $CH_2CH_2OH$, $OH$ or $OMe$;

$R^5$ represents hydrogen or methyl;

Y represents hydrogen or a hydrogen bond donating group, such as $NHSO_2Me$, $NHCO_2Me$, $NH_2$, $CH_2OH$, $B(OH)_2$, $CONH_2$, $SO_2NH_2$, or preferably $OH$;

X represents oxygen, sulfur, NH, N ($C_1$–$C_5$ lower alkyl), N(acyl), $CH_2$, CO, SO, $SO_2$;

$n_1$ is 1–2, preferably 2; and $n_2$ is 1–2, preferably 2.

The present invention also provides prodrugs of the compounds of Formula II which prodrugs have the general structural Formula (III)

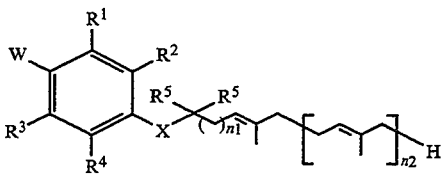

wherein

W is a physiologically hydrolyzable ester, preferably an ester of phenol such as acetate, nicotinate, or succinate; and $R^1$, $R^2$, $R^3$, $R^4$, $R^5$, X, $n_1$ and $n_2$ are as described in Formula II.

The all cis (E), all trans (Z), or a cis/trans mixture of the olefin units in the polyprenyl side chain of the compounds of Formulas II and III are specifically included within the scope of this invention.

Also included within the scope of the present invention are the pharmaceutically acceptable acid addition salts, the metal salts, and the solvates of the compounds of Formulas II and III which may exist in various tautomeric forms.

The term "$C_1$–$C_5$ lower alkyl" as used herein and in the claims (unless the context indicates otherwise) mean unbranched or branched chain alkyl groups such as methyl, ethyl, propyl, isopropyl, butyl, isobutyl, t-butyl, etc. Preferably those groups contain from 1 to 5 carbon atoms and, most preferably, they contain one atom. Unless otherwise specified in the particular instance, the term "halogen" as used herein and in the claims is intended to include chloride, bromide, fluoride, and iodide.

The term "prodrug" as used herein and in the claims (unless the context indicates otherwise) denotes an analog of an active drug which is converted after administration back to the active drug. More particularly, it refers to analogs of acyclic tocotrienols which are capable of undergoing hydrolysis of the ester moiety or oxidative cleavage of the ester moiety so as to release active, free drug. The physiologically hydrolyzable esters serve as prodrugs by being hydrolyzed in the body to yield the parent drug per se.

Synthesis of Acyclic Tocotrienol Analogs

The majority of the farnesylated aromatic compounds were prepared in a straightforward manner either by coupling of the phenol with farnesylethanol mediated by diethylazodicarboxylate/triphenylphosphine (Mitsunobu, O. *Synthesis*, 66 (1983)) (see Table 1), or by alkylation of the aromatic moiety with the appropriate farnesylated side chain halide, (see Table 2). In some cases, the desired test compounds were obtained after deprotection, these are shown in Table 3.

Additional test compounds (for example, the compounds of Example number 24, 25, 22, 26, 14, 27, 17, 18, 31, and 32) were prepared from given examples using straightforward oxidation and/or reduction and/or alkylation and/or acylation procedures and are detailed in the experimental section. (See Table 3)

TABLE 1

Farnesylated Aromatic Compounds Prepared By Mitsunobu Coupling

| Aromatic Substitution | Yield % |
|---|---|
| H | 77 |
| 4-OAc | 52 |
| 3-OAc | 33 |
| 2-OAc | 38 |
| 2,6-Me; 4-OCOPh | 89 |
| 2,6-OMe; 4-OCOtBu | 96 |
| 2,3,6-Me; 4-OCOPh | 83 |
| 2,3,5,6-F; 4-OAc | 60 |
| 2-COMe; 4-OAc | 38 |
| 2(3H)-Benzofuranone-5-Yl | 20 |
| 4-CONH$_2$ | 75 |
| 4-Br | 66 |
| 4-NO$_2$ | 67 |
| 2,6-Me; 4-NO$_2$ | 91 |
| 4-SO$_2$NH$_2$ | 43 |
| 3-CO$_2$Me | 89 |

TABLE 2

Farnesylated Aromatic Compounds Prepared By Alkylation

| Aromatic Substitution | n | Y | % Yield |
|---|---|---|---|
| 2,3-Me; 4-OCOPh | 2 | O | 32 |
| 2,3-Me; 4-OCOPh | 3 | O | 55 |
| 2,6-Me; 4-OSiMe$_2$tBu | 3 | O | 55 |
| 4-CH$_2$OH | 3 | O | 20 |
| 4-OH | 3 | S | 76 |

The nitrogen-linked examples (compounds of Examples 37 and 36) were prepared as shown in Scheme 1. Para-aminophenol was acylated as its mono t-butoxycarbamate and the phenol silylated to give the crystalline carbamate, which was alkylated with farnesylethyl iodide then deprotected to give the compound of Example 37. The compound of Example 36 was prepared as shown in Scheme 1 by the reductive amination of farnesylacetaldehyde with para-aminophenol.

a metalation/alkylation sequence (Scheme 2). It was our original intention to obtain the compound of Example 33 from this route by reduction of either the compound of Example 34 or the compound of Example 35. However, we were unable to obtain in pure form the desired compound from either the dithiane or the ketone by reductive methods. The methylene linked, compound of Example 33, was obtained using the procedure outlined in Scheme 3.

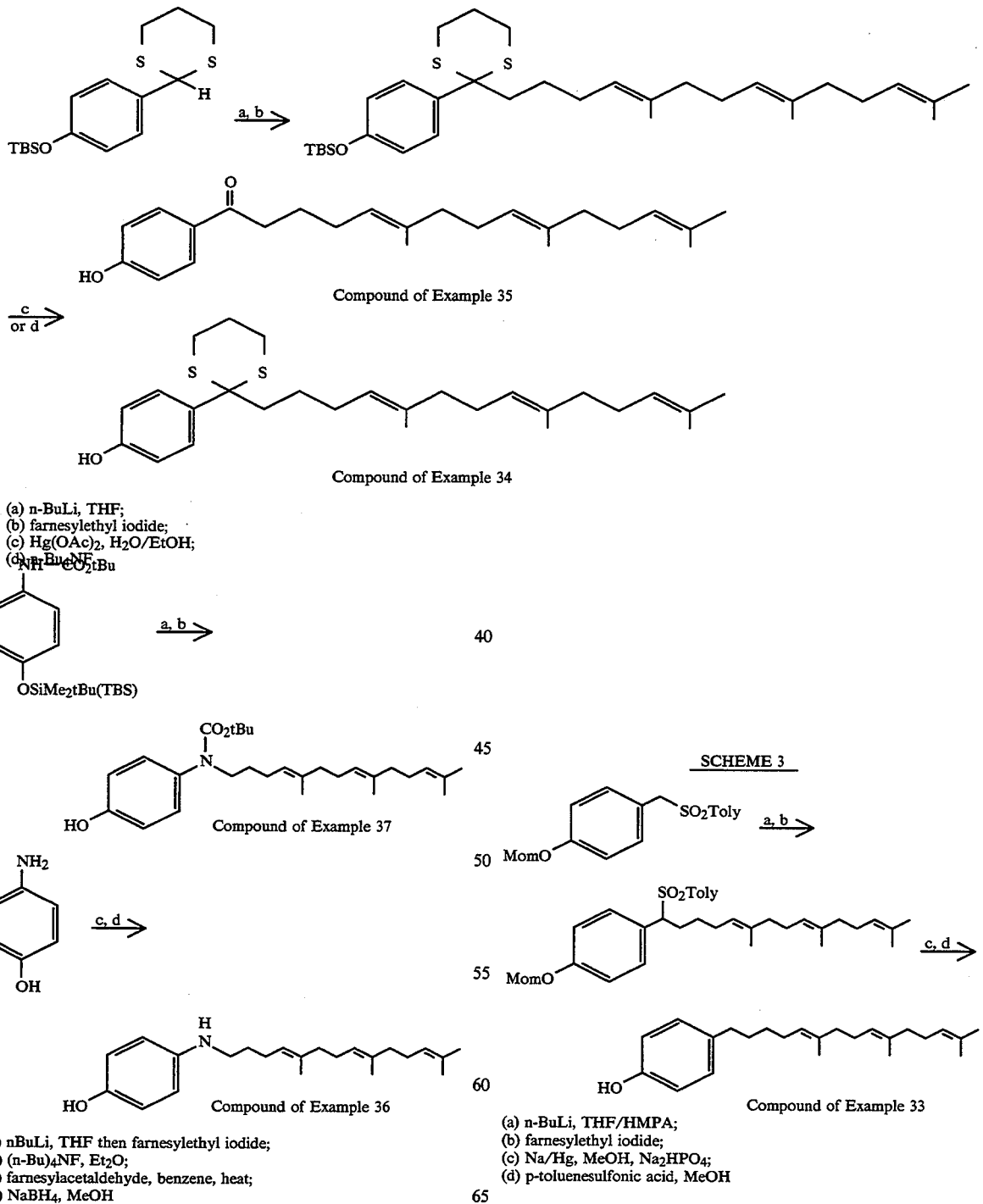

The compounds of Examples 34 and 35 were prepared from the silylated 4-(1,3-dithian-2-yl)phenol using The compounds of Examples 38 and 39 were prepared from the farnesyl acetone as shown in Scheme 4.

SCHEME 4

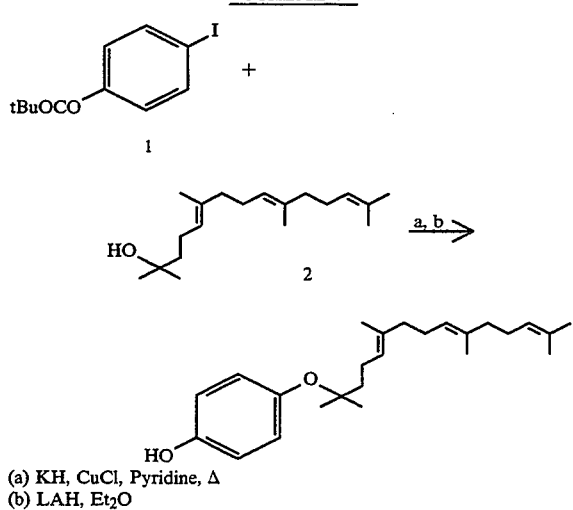

(a) KH, CuCl, Pyridine, Δ
(b) LAH, Et₂O

TABLE 3

| Aromatic Substitution | n | X | R⁵ | Compound of Example |
|---|---|---|---|---|
| H-Unsubstituted | 2 | O | H | 5 |
| 2-OH | 2 | O | H | 6 |
| 3-OH | 2 | O | H | 7 |
| 4-OH | 2 | O | H | 8 |
| 2,3-Me; 4-OH | 1 | O | H | 10 |
| 2,3-Me; 4-OH | 2 | O | H | 11 |
| 2,6-Me; 4-OH | 2 | O | H | 12 |
| 2,6-Me; 4-OH | 2 | O | H | 13ᵃ |
| 2,6-Me; 4-OCONH₂ | 2 | O | H | 14 |
| 2,3,6-Me; 4-OH | 2 | O | H | 15 |
| 2,6-OMe; 4-OH | 2 | O | H | 16 |
| 2,6-Me; 3,5-CH₂OH; 4-OH | 2 | O | H | 17 |
| 3-CH₂CH₂OH; 4-OH | 2 | O | H | 18 |
| 2,3,5,6-F; 4-OH | 2 | O | H | 19 |
| 2-COMe; 4-OH | 2 | O | H | 20 |
| 4-CH₂OH | 2 | O | H | 21 |
| 3-CH₂OH | 2 | O | H | 22 |
| 4-CONH₂ | 2 | O | H | 23 |
| 4-NH₂ | 2 | O | H | 24 |
| 4-NHSO₂Me | 2 | O | H | 25 |
| 2,6-Me; 4-NH₂ | 2 | O | H | 26 |
| 2,6-Me; 4-NHCO₂Me | 2 | O | H | 27 |
| 4-SO₂NH₂ | 2 | O | H | 28 |
| 4-B(OH)₂ | 2 | O | H | 29 |
| 4-OH | 2 | S | H | 30 |
| 4-OH | 2 | SO | H | 31 |
| 4-OH | 2 | SO₂ | H | 32 |
| 4-OH | 2 | CH₂ | H | 33 |
| 4-OH | 2 | 1,3-dithian-2-yl | H | 34 |
| 4-OH | 2 | CO | H | 35 |
| 4-OH | 2 | NH | H | 36 |
| 4-OH | 2 | N CO₂tBu | H | 37 |
| 4-OH | 1 | O | CH₃ | 39 |

ᵃside chain E, Z mixture

BIOLOGICAL DATA

The biological activity of the compounds of Formulas II and III may be demonstrated in the following biological tests.

HepG2 Cell Culture Model—14C-Acetate Incorporation Assay

HepG2 cells obtained from the American Type Culture Collection were routinely passaged in RPMI-1640 plus 10% fetal bovine serum (FBS) and were subcultured into 35 mm diameter wells for experiments. At approximately 60–70% confluence, the medium was changed to 2.0 ml RPMI-1640 plus 7% lipid-depleted serum (LDS) to induce cholesterogenesis as suggested by Burki et al., *J. Lipid Res.*, 28: 1199–1205, (1987). The LDS medium supplement was prepared according to Cham et al, *J. Lipid Res.*, 17: 176–181, (1976). After 16 hours in LDS containing media, test compounds were added in dimethylsulfoxide vehicle (0.5% v/v final conc.) for an incubation period of 3–4 hours. Cholesterol synthesis was then directly determined by 2-14C-acetate (1.8 mCi/mmol, 0.5 μCi/ml) incorporation for 30 to 60 minutes (previously shown to be time-linear) into total digitonin-precipitable sterols. The isolation of this total sterol fraction followed standard methods as described previously (Kates, et al, *North Holland-Amsterdam/-Elsevier-New York*, Techniques of Lipidology, pp. 349, 360–364, (1972); and Ingebritsen et al., *J. Biol. Chem.*, 254: 9986–9989, (1979). Briefly, samples were precipitated and washed with perchloric acid, saponified in 90% methanol/0.30N NaOH, then quantitatively extracted in hexanes to obtain the non-saponifiable lipids. From this fraction the digitonin-precipitable sterols were obtained. Greater than 98% of the 14C content in this fraction was shown by HPLC to co-elute with authentic cholesterol standard. Percent inhibition was calculated from the average of duplicates vs. triplicate vehicle controls conducted simultaneously.

The inhibition of cholesterol biosynthesis in HepG2 cells exhibited by the compounds of the present invention are indicated in Table 4.

TABLE 4

In Vitro Cholesterol Biosynthesis Inhibitory Activity From HepG2 Cells

| Compound of Example | Sterol Biosynthesis % Inhibition 10 μM |
|---|---|
| γ-tocotrienol | 69 |
| 5 | 12 |
| 6 | 10 |
| 7 | 38 |
| 8 | 71 |
| 9 | 36 |
| 10 | 58 |
| 11 | 64 |
| 12 | 70 |
| 13 | 70 |
| 14 | 65 |
| 15 | 48 |
| 16 | 66 |
| 17 | 72 |
| 18 | 64 |
| 19 | 55 |
| 20 | 69 |
| 21 | 64 |
| 22 | 73 |
| 23 | 42 |
| 24 | 65 |
| 25 | 77 |
| 26 | 51 |
| 27 | 47 |
| 28 | 58 |
| 29 | 99 |
| 30 | 68 |
| 31 | 47 |
| 32 | 38 |
| 33 | 50 |
| 34 | 43 |
| 35 | 78 |

TABLE 4-continued

In Vitro Cholesterol Biosynthesis Inhibitory Activity From HepG2 Cells

| Compound of Example | Sterol Biosynthesis % Inhibition 10 μM |
|---|---|
| 36 | 43 |
| 37 | 79 |
| 39 | 37 |

HepG2 Cell Culture Model–HMG-CoA Reductase Suppression Assay

HMG-CoA reductase suppression in HepG2 cells was conducted by growing cells in RPMT-1640 plus 10% FBS on 100 mm plates, and when cells reached approximately 75% confluency, inducing with LDS (as described above) for 16 hours prior to assays. Compounds were added using dimethylsulfoxide vehicle (0.5% v/v, final) and after 4 hours of incubation at 37°, cells were harvested by scraping. Cell pellets were rinsed and lysed by sonication in 1.7 ml cold 50 mM imidazole-HCl, pH 7.2, 50 mM NaCl, 10 mM EDTA, 10 mM EGTA, 5 mM DTT, and 40 μM leupeptin). Lysates were centrifuged at 150×g and the supernatant was centrifuged at 100,000×g in a Beckman airfuge to isolate the post-nuclear total membrane fraction. The membranes were resuspended in 50 mM imidazole-HCl, pH 7.2, 250 mM NaCl, 5 mM DTT, and 20 μM leupeptin and used for the assay of HMG-CoA reductase activity by the radiochemical procedure as described previously by Parker et al., *J. Biol. Chem.*, 264: 4877–4887, (1989). Values were normalized for protein content by the Lowry method as cited previously (ibid). HMG-CoA reductase percent suppression was calculated as the decrease in specific activity of HMG-CoA reductase for treated cells vs. controls receiving vehicle. Averages of duplicate cell determinations assayed in duplicate were taken.

The suppression of HMG-CoA reductase in HepG2 cells exhibited by the compounds of the present invention are indicated in Table 5.

TABLE 5

In Vitro HMG-CoA Reductase Suppression From HepG2 Cells

| Compounds of Example | HMG-CoA Reductase Suppression % 10 μM |
|---|---|
| γ-Tocotrienol | 63 |
| 8 | 29 |
| 10 | 38 |
| 11 | 53 |
| 12 | 35 |
| 13 | 45 |
| 14 | 21 |
| 21 | 9 |
| 25 | 9 |
| 30 | 29 |

In Vivo Biological Evaluation in Normocholesterolemic Chickens

Newborn male chicks (10 for each group) were raised on a standard corn-soybean based control diet for two weeks and then switched to either control or experimental diets for four weeks. Drug treatment consisted of the addition of test compounds to the corn-soybean-based diet at a concentration of 50 ppm. At the end of the feeding period, all the birds were fasted (36 hours) and refed (48 hours) to induce cholesterolgenic enzymes prior to sacrifice. The specific activity of HMGR, total serum cholesterol levels, LDL cholesterol and HDL cholesterol pools were determined (Table 6).

TABLE 6

Effects of test compound and γ-tocotrienol on Lipid Metabolism in 6-week old male chickens Values Given As % of Control

| Compound of Example | Total Cholesterol | LDL Cholesterol | HDL Cholesterol | HMGR |
|---|---|---|---|---|
| 12 | 67 | 50 | 70 | —a |
| 25 | 72 | 45 | 91 | 86 |
| γ-Tocotrienol | 75 | 44 | 91 | 82 | a - not done

The results to the above tests demonstrates that the compounds of Formulas II and III inhibit HMGR activity which results in a decrease in serum total cholesterol and LDL cholesterol levels.

Thus, the compounds of Formulas II and III may be readily administered, to treat hypercholesterolemia, hyperlipidemia, and atherosclerosis, in avian and mammalian systems in need of such treatment. For this purpose, the drug may be administered by conventional routes including, but not limited to, the alimentary canal in the form of oral doses, or by injection in sterile parenteral preparations.

In yet another aspect, the present invention provides a pharmaceutical composition which comprises a compounds of Formula II or III and a non-toxic pharmaceutically acceptable carrier or diluent. These carriers can be solid or liquid such as cornstarch, lactose, sucrose, olive oil or sesame oil. If a solid carrier is used, the dosage forms may be tablets, capsules, powders, troches or lozenges. If the liquid form is used, soft gelatin capsules, syrup or liquid suspensions, emulsions, or solutions in convenient dosage forms may be used. The composition may be made up of any pharmaceutical form appropriate for the desired route of administration. Examples of such compositions include solid compositions for oral administration such as tablets, capsules, pills, powders and granules, liquid compositions for oral administration such as solutions, suspensions, syrups or elixirs and preparations for parenteral administration such as sterile solutions, suspensions or emulsions. They may also be manufactured in the form of sterile solid compositions which can be dissolved in sterile water, physiologically saline or some other sterile injectable medium immediately before use.

The dosage ranges will commonly range from about 50 mg to about 200 mg. Optimal dosages and regimes for a given host can be readily ascertained by those skilled in the art. It will, of course, be appreciated that the actual dose used will vary according to the particular composition formulated, the particular compound used, the disease being treated. Many factors that modify the action of the drug will be taken into account including age, weight, sex, diet, time of administration, route of administration, rate of excretion, condition of the patient, drug combinations, reaction sensitivities and severity of the disease.

CHEMISTRY EXPERIMENTAL

The following examples are intended for illustrative purpose only and are not to be construed as limiting the invention in sphere or scope.

All temperatures are understood to be in degrees in C when not specified. Melting points were recorded on a Thomas-Hoover melting point apparatus and are uncorrected. Boiling points are uncorrected. Infrared spectra were obtained on a Perkin-Elmer Model 1800 FT-IR spectrophotometer. $^1$H-NMR spectra were recorded on a Bruker AM 300 spectrometer or a Varian Gemini 300 NMR spectrometer; nuclear magnetic resonance (NMR) spectral characteristics refer to chemical shifts ($\delta$) expressed in parts per million (ppm) with tetramethylsilane (TMS) as an internal standard. The relative area reported for the various shifts in the proton NMR spectral data corresponds to the number of hydrogen atoms of a particular functional type in the molecule. The nature of the shifts as to multiplicity is reported as broad singlets (br s), singlets (s), multiplet (m), doublet (d), doublet of doublets (dd), triplet (t), or quartet (q). Mass spectra were measured on a Finnegan 4500 spectrometer (low resolution) or a Kratos MS50 spectrometer (high resolution).

Thin-layer chromatography was performed on silica gel 60 F-254 plates purchased from E. Merck and company (visualization with iodine or phosphomolybdic acid); flash chromatography was performed on fine silica (EM Sciences, 230–240 mesh). HPLC analyses were performed on a Spectra-Physics apparatus. All reactions were run under dry nitrogen unless otherwise indicated. Dry solvents were purchased from Aldrich, Milwaukee, Wis. in sure/seal bottles and transferred by syringe under nitrogen. Most commercially available starting materials did not require further purification.

EXAMPLE 1

Starting Material—Farnesylethanol

Lithium diisopropylamide (THF complex, 124 mL, 0.19 mole, 1.5M cyclohexane) was added dropwise to a $-78°$ C. solution of t-butyl acetate (21.6 g, 0.19 mole) in dry THF (200 mL) under nitrogen. The mixture was stirred for about 1 hour at about $-78°$ and then a THF solution (50 mL) of freshly prepared farnesyl bromide (51.3 g, 0.18 mole) was added dropwise to the lithium enolate. The mixture was slowly warmed to about 23° over 18 hours and quenched with aqueous NH$_4$Cl. The solution was poured into water and extracted with ether. The ether extracts were dried (brine, MgSO$_4$) and concentrated in vacuo. The crude ester was purified by flash chromatography (10:1 Hexanes: Ether) and Kugelrohr distillation (bath 125°–140°/0.05 mm) to yield the t-butyl ester (35.8 g, 0.11 mole, 62%) as a pale yellow oil: IR (film) 2979, 2920, 1730, 1450, 1365 cm$^{-1}$; $^1$H NMR (CDCl$_3$) $\delta$ 1.40 (s, 9H), 1.55 (s, 3H), 1.56 (s, 3H), 1.59 (s, 3H), 1.65 (s, 3H), 1.91–2.04 (m, 8H), 2.18–2.25 (m, 4H), 5.07 (m, 3H); MS m/e=321 (MH+). Anal. calcd. for C$_{21}$H$_{36}$O$_2$:C, 78.70; H, 11.32. Found:C, 78.95; H, 11.09.

An ether solution (200 mL) of the t-butyl ester (42.5 g, 0.13 mole) was added dropwise to a suspension of lithium aluminum hydride (10.1 g, 0.26 mole) in ether (200 mL) at 0° C. under nitrogen. The mixture was stirred for about 1 hour at about 0° then quenched with 1N HCl (caution) until the mixture was just acidic. The reaction mixture was poured into water and extracted with fresh ether. The ether extracts were dried (brine, MgSO$_4$) and concentrated in vacuo. The crude alcohol was purified by flash chromatography (5:1 Hexanes: Ether) followed by Kugelrohr distillation (bath 110–115°/0.2 mm) to yield the purified farnesylethanol (30.4 g, 0.12 mole, 94%) as a colorless oil: IR (film) 3336, 2928, 1446 cm$^{-1}$; $^1$H NMR (CDCl$_3$) $\delta$ 1.57 (s, 3H), 1.59 (s, 3H), 1.62–1.69 (m, 2H), 1.65 (s, 3H), 1.95–2.10 (m, 10H), 3.62 (t, J=6.5 Hz, 2H), 5.05–5.15 (m, 3H); MS m/e 251 (MH+). Anal. calcd. for C$_{17}$H$_{30}$O$_1$, 0.5 H$_2$O: C, 78.70; H, 12.05. Found: C, 79.03; H, 12.12.

EXAMPLE 2

Starting Material—Farnesylethyl Iodide

Methanesulfonyl chloride (3.3 mL, 42 mmole) in 50 mL of CH$_2$Cl$_2$ was added dropwise to a solution of farnesylethanol (10.0 g, 40 mmole) and triethylamine (6.1 mL, 44 mmole) in CH$_2$Cl$_2$ (100 mL) at about 0° under nitrogen. The mixture was stirred for about 1 hour at about 0°, then for about 1 hour at about 23°. The solution was poured into water and extracted with CH$_2$Cl$_2$. The organic extracts were dried (MgSO$_4$) and concentrated in vacuo giving a yellow oil which was used directly in the next step.

The mesylate was added to a suspension of sodium iodide (60 g, 400 mmole) in acetone (300 mL) and the mixture was heated to reflux for about 1 hour. The solution was poured into water and extracted with ether. The organic extracts were dried (brine, MgSO$_4$) and concentrated in vacuo to give a dark oil which was purified by flash chromatography (hexanes) to give farnesylethyl iodide (13.3 g, 92%) as a colorless oil. A sample of the iodide was distilled in a Kugelrohr oven (bath 110–115/0.05 mm) for analysis: IR (film) 2926, 1446, 1382, 1228, 1202 cm$^{-1}$; $^1$H NMR (CDCl$_3$) $\delta$ 1.58 (s, 6H), 1.62 (s, 3H), 1.66 (s, 3H), 1.84 (m, 2H), 1.90–2.10 (m, 10H), 3.16 (t, J=6.9 Hz, 2H), 5.07 (m, 3H); MS/me 361 (MH+). Anal. calcd. for C$_{17}$H$_{29}$I$_1$: C, 56.67; H, 8.11. Found: C, 56.36; H, 8.00.

EXAMPLE 3

General Procedure for Coupling via Alkylation

A mixture of the phenol (3 mmole), farnesylethyl iodide (3 mmole), and micropulverized anhydrous potassium carbonate (6 mmole) was stirred under nitrogen in about 8 mL of dry acetonitrile. The mixture was stirred at room temperature or heated to reflux as required for completion. The mixture was then poured into 1N HCl and extracted into ether. The ether extracts were dried (brine, MgSO$_4$) and concentrated in vacuo to yield the crude alkylation products, which were purified by flash chromatography. Analytical samples were prepared by vacuum distillation of the purified products in a Kugelrohr oven.

EXAMPLE 4

General Procedure for the Mitsunobu Coupling

A mixture of the phenol (10 mmole), farnesylethanol (10 mmole) and triphenyphosphine (11 mmole) were dissolved in about 10 mL of dry THF under nitrogen. Diethyl azodicarboxylate (11 mmole) was added dropwise to the stirred THF solution and the mixture was stirred for about 18 hours at about 23° C. The solvent was removed in vacuo and the crude material was triturated with hexanes. The solid residue was removed by filtration, and the filtrate was concentrated in vacuo to an oil. The crude oils were purified by flash chromatography and when appropriate were vacuum distilled in a Kugelrohr oven for analysis.

EXAMPLE 5

(5,9,13-Trimethyl-4(E), 8(E), 12-tetradecatrienyl)oxy benzene

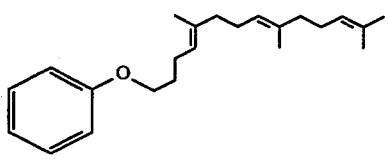

The compound of the present Example was prepared as indicated in Example 4 using the Mitsunobu method to couple phenol and farnesylethanol (77%). The crude material was purified by flash chromatography followed by distillation to yield a colorless oil [Kugelrohr oven (bath 160°-170°/0.08 mm)]: IR (film) 2924, 1600, 1588, 1498, 1246, 752 cm$^{-1}$; $^1$H NMR (CDCl$_3$) δ 1.58 (s, 9H), 1.66 (s, 3H), 1.81 (m, 2H), 1.90-2.10 (m, 8H), 2.16 (q, J=7.2 Hz, 2H), 3.93 (t, J=6.4 Hz, 2H), 5.08 (m, 2H), 5.15 (m, 1H), 6.90 (m, 3H), 7.25 (m, 2H); MS m/e 326 (M+).

Anal. calcd. for C$_{23}$H$_{34}$O$_1$: C, 84.61; H, 10.50. Found: C, 84.71; H, 10.72.

EXAMPLE 6

2-[(5,9,13-Trimethyl-4(E), 8(E),12-tetradecatrienyl)oxy]phenol

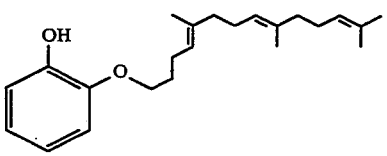

The compound of the present Example was prepared using the Mitsunobu method (Example 4) from catechol monoacetate (Anchisi et al, *J. Het. Chem.*, 39:141-142 (1982)) (37%). The ester was saponified using about 10 mL of 0.5N methanolic KOH under a nitrogen atmosphere for about 1 hour at 23° C., to give the compound of the present Example as a yellow oil (89%) which was distilled in a Kugelrohr oven (bath 150°-160°/0.1 mm) providing a pale yellow oil: IR (film) 3548, 2926, 1502, 1260, 1224, 1108, 742 cm$^{-1}$; $^1$H NMR (CDCl$_3$) δ 1.58 (s, 9H), 1.66 (s, 3H), 1.84 (m, 2H), 1.90-2.10 (m, 8H), 2.15 (q, J=7.2 Hz, 2H), 4.00 (t,J=6.4 Hz, 2H), 5.08 m,2H), 5.14 (m, 1H), 5.62 (s, 1H), 6.80-6.92 (m, 4H); MS m/e 342 (M+) . Anal. calcd. for C$_{23}$H$_{34}$O$_2$: C, 80.65; H, 10.00. Found: C, 80.71; H, 10.05.

EXAMPLE 7

3-[(5,9,13-Trimethyl-4(E), 8(E), 12-tetradecatrienyl)oxy]phenol

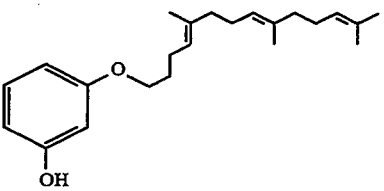

The compound of the present Example was prepared in the same manner as the compound of Example 6 from resorcinol monoacetate (33%). Saponification gave the compound of the present Example as a colorless oil (95%) which was distilled in a Kugelrohr oven (bath 170°-180°/0.15 mm) providing a colorless oil: IR (film) 3406, 2928, 1596, 1494, 1458, 1286, 1176, 1150, 764 cm$^{-1}$; $^1$H NMR (CDCl$_3$) δ 1.57 (s, 9H), 1.66 (s, 3H), 1.78 (m, 2H), 1.90-2.10 (m, 8H), 2.13 (q, J=7.2 Hz, 2H), 3.89 (t, J=6.4 Hz, 2H), 4.81 (s, 1H), 5.07 (m, 2H), 5.13 (m, 1H), 6.38 (m, 2H), 6.45 (d, J=8.3 Hz, 1H), 7.09 (m, 1H); MS m/e 343 (MH+). Anal. calcd. for C$_{23}$H$_{34}$O$_2$: C, 80.65; H, 10.00. Found: C, 80.57; H, 10.36.

EXAMPLE 8

4-[(5,9,13-Trimethyl-4(E), 8(E),12-tetradecatrienyl)oxy]phenol

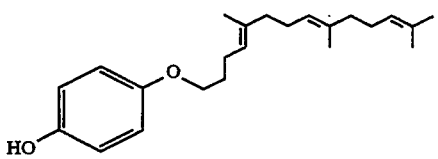

The monoacetate of the compound of the present Example was prepared from hydroquinone monoacetate (Johnston, D. *Chem. Ind.*, 24: 1000, (1984)) using the Mitsunobu method (51%). The ester was saponified in the manner described for the compound of Example 6 to yield the compound of the present Example (86%) as a colorless oil [Kugelrohr oven (bath 170°-180°/0.15 mm)]: IR (film): 3400, 2940, 1510, 1450, 1230, 780 cm-$^1$; $^1$H NMR (CDCl$_3$) δ 1.58 (s, 9H), 1.66 (s, 3H), 1.78 (m, 2H), 1.90-2.10 (m, 8H), 2.14 (q. J=7.2 Hz, 2H), 3.87 (t, J=6.5 Hz, 2H), 4.54 (s, 1H), 5.05-5.16 (m, 3H), 6.75 (m, 4H); MS m/e 342 (M+). Anal. calcd. for C$_{23}$H$_{34}$O$_2$: C, 80.65; H, 10.00. Found: C, 80.46; H, 10.10.

EXAMPLE 9

2,3-Dimethyl-4-[(3,7,11-Trimethyl-2(E), 6(E), 10-dodecatrienyl)oxy]phenol

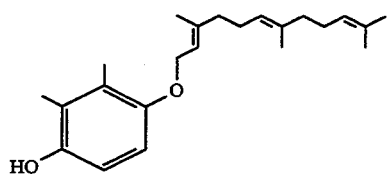

2,3-Dimethylhydroquinone monobenzoate (Mayer, et al, *Methods in Enzymology;* Colowick, S. P.; Kaplan, N. O. Ed.; Academic Press, New York, 1971, Vol. XVIII, p. 296) was alkylated with farnesyl bromide using the general procedure (Example 3) described (91%). The benzoate (1.87 mmole, 835 mg) was saponified in about 10 mL of 0.5N methanolic KOH. The mixture was stirred for about 1 hour at about 23° C. then poured into 1N HCl and extracted into ether. The ether extracts were dried (brine, MgSO$_4$) and concentrated in vacuo to give an oil which was purified by flash chromatography (8:1 hexanes: ether). The resulting oil (626 mg, 1.83 mmole, 98%) crystallized on standing and was recrystallized from pentane to give white fluffy crystals, m.p. 39°-40°: IR (KBr) 3350, 2940, 1500, 1255, 1100, 798, cm-$^1$; $^1$H NMR (CDCl$_3$) δ 1.58 (s, 6H), 1.66 (s, 3H), 1.69 (s, 3H), 1.92-2.15 (m, 8H), 2.15 (s, 6H), 4.32

(br s, 1H), 4.43 (d, J=6.3 Hz, 2H), 5.07 (m, 2H), 5.47 (m, 1H), 6.55 (d, J=8.7 Hz, 1H), 6.60 (d, J=8.7 Hz, 1H); MS m/e 342 (M+). Anal. calcd. for $C_{23}H_{34}O_2$: C, 80.65; H, 10.00. Found: C, 80.78; H, 10.10.

EXAMPLE 10

2,3-Dimethyl-4-[(4,8,12-Trimethyl-3(E), 7(E), 11-tridecatrienyl)oxy]phenol

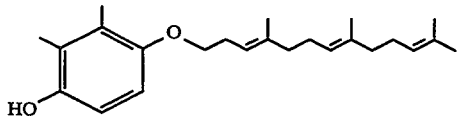

The compound of the present Example was prepared in the same manner as the compound of Example 9 using homofarnesyl iodide (Kocienski, P.; Wadman, S. J. Org. Chem., 54: 1215-1217 (1989)) (32%). Saponification of the benzoate ester gave the compound of the present Example (55%) as a colorless oil which was distilled in a Kugelrohr oven (bath 140°-150°/0.2 mm): IR (film) 3406, 2920, 1488, 1462, 1248, 1102, 758 cm$^{-1}$; $^1$H NMR (CDCl$_3$) δ 1.58 (s, 6H), 1.64 (s, 3H), 1.66 (s, 3H), 1.90-2.10 (m, 8H), 2.15 (s, 6H), 2.45 (q, J=7.2 Hz, 2H), 3.83 (t, J=7.0 Hz, 2H), 4.35 (s, 1H), 5.08 (m, 2H), 5.22 (t, J=7.2 Hz, 1H), 6.56 (m, 2H); MS m/e 357 (MH+). Anal. calcd. for $C_{24}H_{36}O_2$: C, 80.85; H, 10.18. Found: C, 80.56; H, 10.12.

EXAMPLE 11

2,3-Dimethyl-4-[(5,9,13-Trimethyl-4(E), 8(E), 12-tetradecatrienyl)oxy]phenol

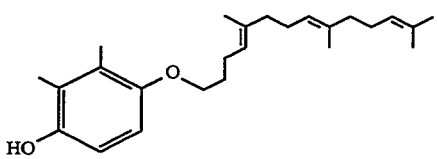

The benzoate ester of the present Example was prepared in the same manner as that described for the benzoate ester of the compound of Example 9 except farnesylethyl iodide was used instead of farnesyl bromide. The benzoate ester was isolated as a colorless oil: IR (film) 2930, 1740, 1485, 1470, 1455, 1265, 1230, 1205, 1105, 715, cm$^{-1}$; $^1$H NMR (CDCl$_3$) δ 1.58 (s, 6H), 1.59 (s, 3H), 1.66 (s, 3H), 1.82 (m, 2H), 1.90-2.10 (m, 10H), 2.10 (s, 3H), 2.18 (s, 3H), 3.92 (t, J=6.2 Hz, 2H), 5.08 (m, 2H), 5.17 (m, 1H), 6.70 (d, J=8.8 Hz, 1H), 6.89 (d, J=8.8 Hz, 1H), 7.49 (m, 2H), 7.62 (m, 1H), 8.20 (d, J=7.2 Hz, 2H); MS m/e 475 (MH+).

Anal. calcd. for $C_{32}H_{42}O_3$: C, 80.97; H, 8.92. Found: C, 81.03; H, 9.47.

The benzoate ester was saponified in the same manner as that described for the compound of Example 9 to give the compound of the present Example (97%) as a white solid, mp 51°-53°: IR (KBr) 3300, 2930, 1570, 1250, 1100, 800 cm$^{-1}$; $^1$H NMR (CDCl$_3$) δ 1.56 (s, 9H), 1.66 (s, 3H), 1.78 (m, 2H), 1.90-2.10 (m, 10H). 2.15 (s, 6H), 3.84 (t, J=6.3 Hz, 2H), 4.33 (s, 1H), 5.08 (m, 2H), 5.15 (m, 1H), 6.55 (s, 1H); MS m/e 370 (M+).

Anal. calcd. for $C_{25}H_{38}O_2$. 0.1 H2O: C, 80.64; H, 10.34. Found: C, 80.84; H. 10.33.

EXAMPLE 12

3,5-Dimethyl-4-[(5,9,13-Trimethyl-4(E), 8(E), 12-tetradecatrienyl)oxy]phenol

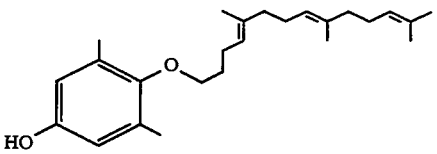

2,6-Dimethyl-1,4-hydroquinone (2.0 g, 14.5 mmole) was silylated with tert-butyldimethylsilyl chloride (2.3 g, 15.2 mmole) and imidazole (1.0 g, 15.2 mmole) in 8 mL of dry DMF. The mixture was stirred for about 1 hour at about 23°, then poured into water. The product was extracted with ether and the organic extracts dried (brine, MgSO$_4$) and concentrated in vacuo. The crude product was purified by flash chromatography to provide a white, solid (2.0 g, 7.4 mmole, 55%), mp 69°-71° C. $^1$H NMR (CDCl$_3$) δ 0.13 (s, 6H), 0.94 (s, 9H), 2.16 (s, 6H), 6.45 (s, 2H).

The silylated hydroquinone was coupled via the alkylation method described in Example 3. The crude product was purified by flash chromatography (50:1 hexanes: ether) to yield a colorless oil (48% yield): $^1$H NMR (CDCl$_3$) δ 0.14 (s, 6H), 0.94 (s, 9H), 1.57 (s, 6H), 1.59 (s, 3H), 1.66 (s, 3H), 1.78 (m, 2H), 1.90-2.10 (m, 8H), 2.15 (m, 2H), 2.16 (s, 6H), 3.67 (t, J=6.4 Hz, 2H), 5.08 (m, 2H), 5.14 (m, 1H), 6.43 (s, 2H).

The silyl ether (620 mg, 1.28 mmole) was dissolved in 6 mL of ether and the solution was cooled to about 0° under nitrogen. Tetra-n-butylammonium fluoride (1.4 mL, 1.0M in THF) was added dropwise to the mixture. After stirring at about 0° for about 1 hour the solution was poured into water and extracted with ether. The organic extracts were dried (brine, MgSO$_4$) and concentrated in vacuo to give a crude material which was purified by flash chromatography (20:1 hexanes: ether) to yield a colorless oil (380 mg, 1.03 mmole, 80%). The oil was distilled in a Kugelrohr oven (bath 200°/0.07 mm) which gave the compound of the present Example as a colorless oil for analysis: IR (film) 3380, 2926, 1600, 1458, 1378, 1318, 1208, 1024, 758 cm$^{-1}$; $^1$H NMR (CDCl$_3$) δ 1.58 (s, 6H), 1.60 (s, 3H), 1.66 (s, 3H), 1.80 (m, 2H), 1.90-2.10 (m, 8H), 2.15 (m, 2H), 2.20 (s, 6H), 3.68 (t, J=6.6 Hz, 2H), 4.45 (s, 1H), 5.08 (m, 2H), 5.15 (m, 1H), 6.45 (s, 2H); MS m/e 371 (MH+). Anal. calcd. for $C_{25}H_{38}O_2$: C, 81.03; H, 10.34. Found: C, 80.99; H, 10.55.

EXAMPLE 13

3,5-Dimethyl-4-[(5,9,13-Trimethyl-4,8, 12-tetradecatrienyl)oxy]phenol

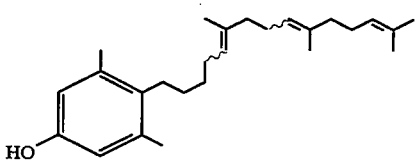

The monobenzoate of the compound of the present Example was prepared from 4-benzoyloxy-2,6-dimethylphenol [mp 138°-140° C.; $^1$H NMR (CDCl$_3$) δ 2.23 (s, 6H), 4.60 (br s, 1H), 6.81 (s, 2H), 7.48 (m, 2H), 7.59

(m, 1H), 8.16 (d, J=8.2 Hz 2H)]and farnesylethanol (mixture of E, Z isomers) using the Mitsunobu method (89%). The ester (10.0 g, 21.1 mmole) was added as an ether solution (10 mL) to a suspension of lithium aluminum hydride (1.2g, 31.6 mmole) in ether (30mL) at about −5° C. After about 30 minutes at about −5°, the solution was carefully quenched with 1N HCl and poured into water. The aqueous mixture was extracted with fresh ether and the organic extracts were dried (brine, MgSO4) and concentrated in vacuo. The resulting oil was distilled in a Kugelrohr over (bath 160°–170°/0.05 mm) giving the compound of the present Example (6.95 g, 18.8 mmole, 89%) as a colorless oil: IR (film) 3388, 2924, 1600, 1452, 1316, 1208, 1024 cm$^{-1}$; $^1$H NMR (CDCl3) δ 1.55–1.68 (m, 12H), 1.80 (m, 2H), 1.90–2.10 (m, 8H), 2.18 (m, 2H), 2.19 (s, 6H), 3.68 (t, J=6.6 Hz, 2H), 4.55 (s, 1H), 5.08 (m, 2H), 5.14 (m, 1H), 6.44 (s, 2H); MS m/e 371 (MH+); HPLC (2-Varian MCH-10 Micro-Pak C18 in line MeCN/H2O gradient) indicated 3 distinct peaks [49.09 min., 13.5%; 50.39 min., 52.4%; 51.94 min., 34.1%]. Anal. calcd. for C25H38O2: C, 81.03; H, 10.34. Found: C, 80.83; H, 10.30.

EXAMPLE 14

3,5-Dimethyl-4-[(5,9,13-Trimethyl-4(E), 8(E), 12-tetradecatrienyl)oxy]phenyl carbamate

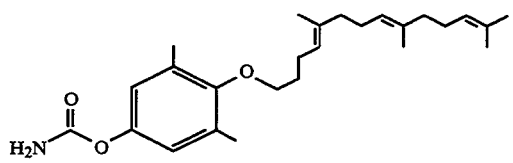

The compound of Example 12 (700 mg, 1.89 mmole) and sodium cyanate (250 mg, 3.78 mmole) were suspended in 10 mL of benzene and a benzene solution (5 mL) of trifluoroacetic acid (450 mg, 3.97 mmole) was added dropwise. The mixture was stirred for about 60 hours at about 23°, then poured into water and extracted into ether. The organic extracts were dried (brine, MgSO4) and concentrated in vacuo to an oil (710 mg). The crude material was purified by flash chromatography (4:1 hexanes: EtOAc) to yield the compound of the present Example (500 mg, 1.21 mmole, 64%) as a colorless oil which crystallized on standing to give a low melting white solid: IR (KBr) 3432, 3268, 2924, 1716, 1474, 1452, 1382, 1368, 1208, 1044 cm$^{-1}$; $^1$H NMR (CDCl3) δ 1.58 (s, 6H), 1.61 (s, 3H), 1.66 (s, 3H), 1.81 (m, 2H), 1.90–2.10 (m, 8H), 2.18 (m, 2H), 2.23 (s, 6H), 3.71 (t, J=6.4 Hz, 2H), 5.04 (br s, 2H), 5.08 (m, 2H), 5.15 (m, 1H), 6.75 (s, 2H); MS m/e 414 (MH+).

Anal. calcd. for C26H39N1O3: C, 75.51; H, 9.50; N, 3.87. Found: C, 75.53; H, 9.66; N, 3.23.

EXAMPLE 15

2,3,5-Trimethyl-4-[(5,9,13-Trimethyl-4(E),8(E), 12-tetradecatrienyl)oxy]phenol

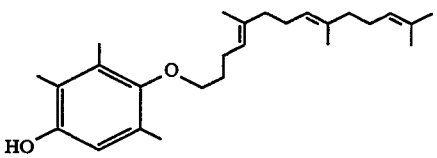

The compound of the present Example was prepared from 4-benzoyloxy-2,3,6-trimethyl phenol [mp 149°–151° C.; $^1$H NMR (CDCl3) δ 2.06 (s, 3H), 2.17 (s, 3H), 2.20 (s, 3H), 4.63 (br s, 1H), 6.75 (s, 1H), 7.50 (m, 2H), 7.62 (m, 1H), 8.20 (d, J=8 Hz, 2H)] following the same procedure as that described for the compound of Example 6. The purified product (51% yield—two steps) was isolated as a colorless oil after Kugelrohr distillation (bath 170°–180°/0.05 mm): IR (film) 3396, 2924, 1450, 1418, 1380, 1224, 1080 cm$^{-1}$; $^1$H NMR (CDCl3) δ 1.59 (s, 6H), 1.62 (s, 3H), 1.67 (s, 3H), 1.82 (m, 2H), 1.90–2.10 (m, 8H), 2.10 (s, 3H), 2.17 (s, 3H), 2.18 (s, 3H), 2.20 (m, 2H), 3.65 (t,. J=6.7 Hz, 2H), 4.59 (br s, 1H), 5.09 (m, 2H), 5.18 (m, 1H), 6.42 (s, 1H); MS m/e 384 (M+). Anal. calcd. for C26H40O2: C, 81.20; H, 10.48. Found: C, 81.52; H, 10.57.

EXAMPLE 16

3,5-Dimethoxy-4-[(5,9,13-Trimethyl-4(E), 8(E), 12-tetradecatrienyl)oxy]phenol

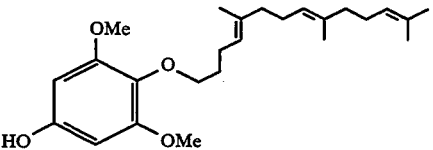

The monopivalate of the compound of the present Example was prepared from 2,6-dimethoxyl-4-pivaloyloxyphenol using the Mitsunobu method (96%), and was isolated as a thick yellow oil: $^1$H NMR (CDCl3) δ 1.35 (s, 9H), 1.59 (s, 6H), 1.60 (s, 3H), 1.67 (s, 3H), 1.79 (m, 2H), 1.90–2.10 (m, 8H), 2.17 (m, 2H), 3.82 (s, 6H), 3.96 (t, J=6.4 Hz, 2H), 5.08 (m, 2H), 5.14 (m, 1H), 6.29 (s, 2H).

The pivalate ester of the compound of the present Example was cleaved with lithium aluminum hydride in the manner described for the compound of Example 13 to yield the compound of the present Example (96%), as a very pale yellow oil after distillation in a Kugelrohr oven (bath 180°–190°/0.04 mm): IR (film) 3364, 2934, 1602, 1508, 1478, 1218, 1196, 1132 cm$^{-1}$; $^1$H NMR (CDCl3) δ 1.58 (s, 6H), 1.59 (s, 3H), 1.66 (s, 3H), 1.80 (m, 2H), 1.90–2.10 (m, 8H), 2.14 (m, 2H), 3.78 (s, 6H), 3.87 (t, J=6.8 Hz, 2H), 4.64 (s, 1H), 5.08 (m, 2H), 5.13 (m, 1H), 6.06 (s, 2H); MS m/e 403 (MH+). Anal. calcd. for C25H38O4: C, 74.59; H, 9.51. Found: C, 74.30; H, 9.37.

EXAMPLE 17

2-Hydroxy-4,6-Dimethyl-5-[(5,9,13-Trimethyl-4(E), 8(E), 12-Tetradecatrienyl)oxy]-1,3-Benzenedimethanol

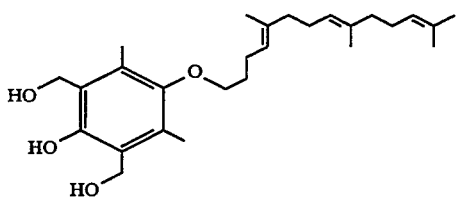

The compound of Example 12 (1.05 g, 2.8 mmole) was dissolved in 10 mL of DMF. To the DMF solution was added 5 mL of aqueous formaldehyde (37%) followed by cesium carbonate (2.0 g, 5.7 mmole) and the mixture was stirred under nitrogen at about 23° for about 12 hours. The solution was poured into water and extracted with ether. The ether extracts were dried (brine, MgSO4) and concentrated in vacuo. The crude material was purified by flash chromatography (gradient 4:1 hexanes: ether to 2:1 ether: hexanes) to yield the compound of the present Example (628 mg, 1.46 mmole, 52%) as a white crystalline solid which was recrystallized from hexanes, mp 107°–108°: IR (KBr) 3244, 2914, 1448, 1380, 1264, 1004 cm$^{-1}$; $^1$H NMR (CDCl3) δ 1.60 (s, 6H), 1.63 (s, 3H), 1.68 (s, 3H), 1.82 (m, 2H), 1.90–2.10 (m, 8H), 2.15 (s, 6H), 2.20 (m, 2H), 2.90 (t, J=5.6 Hz, 2H), 3.59 (t, J=6.6 Hz, 2H), 4.78 (d, J=5.6 Hz, 4H), 5.08 (m, 2H), 5.14 (m, 1H), 8.53 (s, 1H); MS m/e 430 (M+). Anal. calcd. for C27H42O4:C, 75.31; H, 9.83. Found: C, 75.19; H, 9.89.

EXAMPLE 18

2-Hydroxy-5-[(5,9,13-Trimethyl-4(E), 8(E), 12-tetradecatrienyl)oxy]benzene ethanol

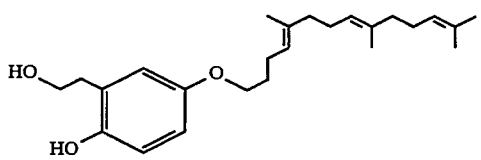

5-[(5,9,13)-Trimethyl-4(E), 8(E), 12-tetradecatrienyl)oxy]-2(3H)-benzofuranone[prepared as indicated in Example 4, white solid, mp 33°–34°: IR (KBr) 2922, 1806, 1488, 1120, 1062, 874 cm$^{-1}$; $^1$H NMR (CDCl3) δ 1.60 (s, 9H), 1.65 (s, 3H), 1.79 (m, 2H), 1.90–2.10 (m, 8H), 2.14 (m, 2H), 3.69 (s, 2H), 3.88 (t, J=6.4 Hz, 2H), 5.06 (m, 2H), 5.13 (m, 1H), 6.80 (m, 2H), 6.97 (d, J=8.6 Hz, 1H); MS m/e 383 (MH+). Anal. calcd for C25H34O3: C, 78.50; H. 8.96. Found: C, 78.54; H, 9.31] (200 mg, 0.52 mmole) was reduced with lithium aluminum hydride in the same manner as the compound of Example 13 to yield the compound of the present Example (150 mg, 0.39 mmole, 75%) as a white solid from pentane, mp 57°–59°: IR (KBr) 3416, 2930, 1508, 1440, 1214, 1040, 1030 cm$^{-1}$; $^1$H NMR (CDCl3) δ 1.57 (s, 9H), 1.66 (s, 3H), 1.76 (m, 2H), 1.90–2.10 (m, 8H), 2.14 (m, 2H), 2.21 (br s, 1H), 8.83 (t, J=5.1 Hz, 2H), 3.86 (t, J=6.5 Hz, 2H), 3.96 (t, J=5.40 Hz, 2H), 5.08 (m, 2H), 5.13 (m, 1H), 6.62 (d, J=2.9 Hz, 1H), 6.68 (d of d, J=8.6, 2.9 Hz, 1H), 6.81 (d, J=8.6 Hz, 1H); MS m/e 386 (M+). Anal. calcd for C25H38O3: C, 77.68; H, 9.91. Found: C, 77.78; H, 10.21.

EXAMPLE 19

2,3,5,6-Tetrafluoro-4-[(5,9,13-Trimethyl-4(E), 8(E)-,12-tetradecatrienyl)oxy]phenol

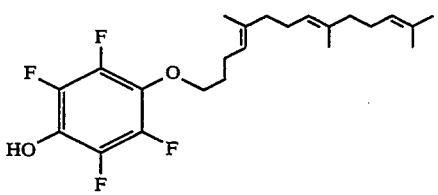

The compound of the present Example was prepared from tetrafluorohydroquinone monoacetate [$^1$H NMR (CDCl3) δ 2.37 (s, 3H), 5.66 (br s, 1H)] following the same procedure as that described for the compound of Example 6. The purified product (51% yield-two steps) was isolated as a pale yellow oil after Kugelrohr distillation (bath 135°–140°/0.15 mm): IR (film) 3400, 2930, 1525, 1505, 1435, 1035, 980 cm$^{-1}$; $^1$H NMR (CDCl3) δ 1.57 (s, 6H), 1.59 (s, 3H), 1.66 (s, 3H), 1.76 (m, 2H), 1.90–2.10 (m, 8H), 2.15 (m, 2H), 4.06 (t, J=6.3 Hz, 2H), 5.08 (m, 3H), 5.66 (br s, 1H); MS m/e 415 (MH+). Anal. calcd. for C23H30F4O2. 0.2 H2O: C, 66.08; H, 7.33; H2O, 0.86. Found: C, 66.10; H, 7.20; H2O, 1.69.

EXAMPLE 20

1-[5-Hydroxy-2-(5,9,13-Trimethyl-4(E), 8(E),12-tetradecatrienyloxy)phenyl]ethanone [BMY 44417]

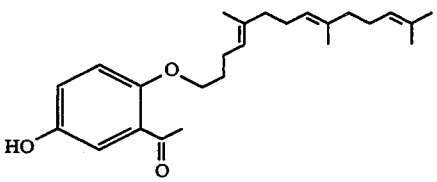

The compound of the present Example was prepared from 5-acetoxy-2-hydroxy-acetophenone [mp 88°–91° C., $^1$H NMR (CDCl3) δ 2.28 (s, 3H), 2.59 (s, 3H), 6.94 (d, J=10 Hz, 1H), 7.18 (d of d, J=10, 3 Hz, 1H), 7.42 (d, J=3 Hz, 1H), 12.10 (s, 1H)] following the same procedure as that described for the compound of Example 6. The purified product (31% yield-two steps) was isolated as a yellow oil after Kugelrohr distillation (bath 180°–184°/0.035 mm): IR (film) 2926, 1658, 1612, 1498, 1446, 1362, 1300, 1216, 586 cm$^{-1}$; $^1$H NMR (CDCl3) δ 1.57 (s, 9H), 1.66 (s, 3H), 1.85 (m, 2H), 1.90–2.10 (m, 8H), 2.17 (q. J=7.2 Hz, 2H), 2.64 (s, 3H), 3.97 (t, J=6.4 Hz, 2H), 5.07 (m, 2H), 5.14 (m, 1H), 5.76 (br s, 1H), 6.82 (d, J=8.9 Hz, 1H), 6.97 (d of d, J=8.9, 3.2 Hz, 1H), 7.33 (d, J=3.2 Hz, 1H); MS m/e 385 (MH+). Anal. calcd. for C25H36O3: C, 78.08; H, 9.44. Found: C, 78.24; H, 9.64.

EXAMPLE 21

4-[(5,9,13-Trimethyl-4(E), 8(E), 12-tetradecatrienyl)oxy]benzenemethanol [BMY 44500]

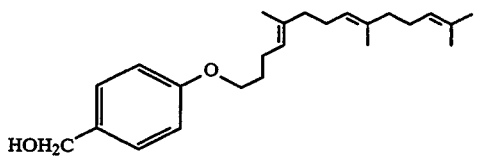

The compound of the present Example was prepared from 4-hydroxybenzyl alcohol using the procedure described in Example 3. The product was isolated as a pale yellow oil (20%) [Kugelrohr oven (bath 180°–190°/0.1 mm)]: IR (film) 3346, 2924, 1512, 1246, 828 cm$^{-1}$; $^1$H NMR (CDCl$_3$) δ 1.50 (t, J=5.7 Hz, 1H), 1.57 (s, 9H), 1.66 (s, 3H), 1.80 (m, 2H), 1.90–2.10 (m, 8H), 2.15 (q, J=7.2 Hz, 2H), 3.92 (t, J=6.4 Hz, 2H), 4.59 (d, J=5.5 Hz, 2H), 5.08 (m, 2H), 5.14 (m, 1H), 6.86 (d, J=8.6 Hz, 2H), 7.25 (d, J=8.6 Hz, 2H); MS m/e 356 (M+).

Anal. calcd. for C$_{24}$H$_{26}$O$_2$: C, 80.85; H, 10.18. Found: C, 80.48; H, 10.24.

EXAMPLE 22

3-[(5,9,13-Trimethyl-4(E), 8(E), 12-Tetradecatrienyl)oxy]benzenemethanol

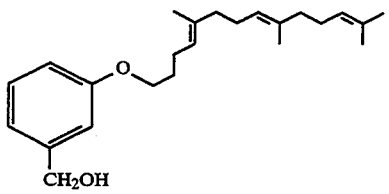

Methyl [3-(5,9,13-trimethyl-4(E), 8(E),12-tetradecatrienyl)oxy]benzoate [prepared as indicated in Example 4, colorless oil (89%)] [Kugelrohr oven (bath 180°/0.4 mm)]: IR (film) 2926, 1726, 1446, 1320, 1288, 1278, 1100, 756 cm$^{-1}$, $^1$H NMR (CDCl$_3$) δ 1.56 (s, 9H), 1.66 (s, 3H), 1.82 (m, 2H), 1.90–2.10 (m, 8H), 2.16 (q, J=7.2 Hz, 2H), 3.89 (s, 3H), 3.96 (t, J=6.4 Hz, 2H), 5.08 (m, 2H), 5.14 (m, 1H), 7.06 (d, J=8.2 Hz, 1H), 7.30 (t, J=8.0 Hz, 1H), 7.52 (s, 1H), 7.59 (d, J=7.7 Hz, 1H); MS m/e 385 (MH+). Anal. calcd. for C$_{25}$H$_{36}$O$_3$: C, 78.08; H, 9.44. Found: C, 78.26; H, 9.18] (2.0 g, 5.21 mmole) was added as an ether solution (5 mL) to a suspension of lithium aluminum hydride (400 mg, 10.42 mmole) in ether (20 mL) at 0°. After about 5 minutes at about 0°, the reaction was quenched with 1N HCl, and poured into water. The product was extracted into ether and the ether extracts were dried (brine, MgSO$_4$) and concentrated in vacuo. The resulting oil was distilled in a Kugelrohr oven (bath 170°–180°/0.15 mm) to yield the compound of the present Example (1.80 g, 5.06 mmole, 97%) as a colorless oil: IR (film) 3336, 2926, 1602, 1586, 1490, 1448, 1264, 1156, 1042, 782 cm$^{-1}$; $^1$H NMR (CDCl$_3$) δ 1.58 (s, 9H), 1.66 (s, 3H), 1.72 (m, 1H), 1.80 (m, 2H), 1.90–2.10 (m, 8H), 2.15 (q, J=7.2 Hz, 2H), 3.93 (t, J=6.4 Hz, 2H), 4.63 (d, J=5.4 Hz, 2H), 5.08 (m, 2H), 5.14 (m, 1H), 6.80 (d, J=8.2 Hz, 1H), 6.90 (m, 2H), 7.23 (t, J=7.6 Hz, 1H)); MS m/e 356 (M+).

Anal. calcd. for C$_{24}$H$_{36}$O$_2$: C, 80.85; H, 10.18. Found: C, 81.12; H, 10.06.

EXAMPLE 23

4-[(5,9,13-Trimethyl-4(E),8(E),12-tetradecatrienyl)oxy]benzamide

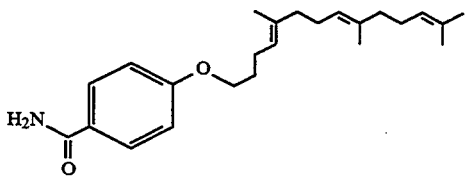

The compound of the present Example was prepared from 4-hydroxybenzamide using the procedure described in Example 4. The product was isolated as a white solid (75%), mp 96°–98° C.: IR (KBr) 3386, 3170, 2912, 1647, 1608, 1572, 1516, 1422, 1390, 1258, 848 cm$^{-1}$; $^1$H NMR (CDCl$_3$) δ 1.57 (s, 9H), 1.65 (s, 3H), 1.84 (m, 2H), 1.90–2.10 (m, 8H), 2.14 (m, 2H), 3.97 (t, J=6.5 Hz, 2H), 5.08 (m, 2H), 5.15 (m, 1H), 6.0 (br s, 2H), 6.90 (d, J=8.9 Hz, 2H), 7.76 (d, J=8.9 Hz, 2H); MS m/e 370 (MH+). Anal. calcd. for C$_{24}$H$_{35}$N$_1$O$_2$: C, 78.01; H, 9.55; N, 3.79. Found: C, 77.77, H, 9.51; N, 3.89.

EXAMPLE 24

4-[(5,9,13-Trimethyl-4(E), 8(E),12-tetradecatrienyl)oxy]aniline

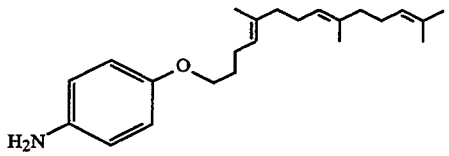

1-Nitro-4-[(5,9,13-trimethyl-4(E), 8(E), 12-tetradecatrienyl)oxy]benzene [prepared as indicated in Example 4, yellow oil (67% )] [Kugelrohr oven (bath 180°–190°/0.15 mm)]: IR (film) 2926, 1608, 1594, 1514, 1498, 1342, 1262, 1112, 846 cm$^{-1}$; $^1$H NMR (CDCl$_3$) δ 1.57 (s, 9H), 1.65 (s, 3H), 1.84 (m, 2H), 1.90–2.10 (m, 8H), 2.16 (q, J=7.2 Hz, 2H), 4.01 (t, J=6.4 Hz, 2H), 5.07 (m, 2H), 5.12 (m, 1H), 6.91 (d, J=9.3 Hz, 2H), 8.16 (d, J=9.3 Hz, 2H); MS m/e 372 (MH+). Anal. calcd. for C$_{23}$H$_{33}$N$_1$O$_3$: C, 74.36; H, 8.95; N, 3.77. Found: C, 74.68; H, 9.04; N, 3.70] (1.0 g, 2.70 mmole) and tin (II) chloride (3.04 g, 13.5 mmole) were dissolved in 15 mL of ethanol and the mixture was heated to about 60° with stirring. Sodium borohydride (51 mg, 1.35 mmole) was added dropwise as an ethanol solution (10 mL) to the mixture. After stirring for about 2 hours at about 60°, the ethanol was removed in vacuo and the residue was treated with water and basified with NaOH. The mixture was extracted with CH$_2$Cl$_2$ and the organic layers were dried (MgSO$_4$). Evaporation to dryness in vacuo yielded 0.9 g of a brown oil which was purified by flash chromatography (3:1 hexanes: ether). The compound of the present Example was recovered as a brown oil (300 mg, 0.88 mmole, 33%) which was further purified by distillation in a Kugelrohr oven (bath 185°–190°/0.1 mm) to give a yellow oil: IR (film) 3450, 3360, 2923, 1512, 1240, 825, 760 cm$^{-1}$; $^1$H NMR (CDCl$_3$) δ 1.57 (s, 9H), 1.66 (s, 3H), 1.76 (m, 2H), 1.90–2.10 (m, 8H), 2.13 (q, J=7.1 Hz, 2H), 3.39 (br s, 2H), 3.84 (t, J=6.5 Hz, 2H), 5.08 (m, 2H), 5.13 (m, 1H), 6.60 (d, J=8.8 Hz, 2H), 6.70 (d, J=8.8 Hz, 2H); MS m/e 341 (M+). Anal. calcd. for $C_{23}H_{35}N_1O_1$: C, 80.89; H, 10.33; N, 4.10. Found: C, 80.64; H, 10.47; N, 3.98.

EXAMPLE 25

N-[4-[(5,9,13-Trimethyl-4(E), 8(E),12-tetradecatrienyl)oxy]phenyl]methanesulfonamide

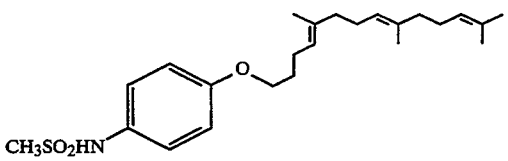

The compound of Example 24 (200 mg, 0.59 mmole) was dissolved in 5 mL of a 5:1 mixture of $CH_2Cl_2$: pyridine. Methanesulfonyl chloride (71 mg, 0.62 mmole) was added dropwise to the aniline derivative and the mixture was stirred for about 1 hour at about 23°. The solution was poured into 1N HCl and extracted with fresh $CH_2Cl_2$. The organic layers were dried ($MgSO_4$) and concentrated in vacuo to give a residue which was purified by flash chromatography (1:1 ether: hexanes) to give the compound of the present Example (220 mg, 0.53 mmole, 89%) as a white, waxy solid. The compound was recrystallized from pentane to give a white solid, mp 61°-63°: IR (KBr) 3252, 2930, 1512, 1320, 1146, 774 cm⁻¹; 1.57 (s 9H) 1.65 (s 3H), 1.79 (m, 2H), 1.90-2.10 (m, 8H), 2.14 (q, J=7.2 Hz, 2H), 3.90 (t, J=6.4 Hz, 2H), 5.08 (m, 2H), 5.13 (m, 1H), 6.46 (br s, 1H), 6.85 (d, J=8.9 Hz, 2H), 7.16 (d, J=8.9 Hz, 2H); MS m/e 420 (MH+). Anal. calcd. for $C_{24}H_{37}N_1O_3S_1$: C, 68.70; H, 8.89; N, 3.34. Found: C, 69.00; H, 9.05; N, 3.34.

EXAMPLE 26

3,5-Dimethyl-4-[(5,9,13-Trimethyl-4(E), 8(E),12-tetradecatrienyl)oxy] aniline

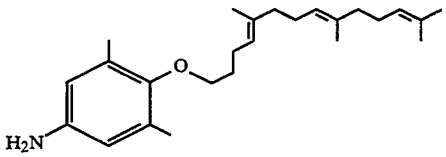

Farnesylethanol was coupled to 2,6-dimethyl-4-nitrophenol in the manner described using the Mitsunobu conditions (91%). After isolation, the nitro aromatic was further purified for analysis by Kugelrohr distillation (bath 160°-180°/0.05 mm) to provide a yellow oil: IR (film) 2924, 1520, 1474, 1446, 1344, 1216, 1098, 702 cm⁻¹; ¹H NMR (CDCl₃) δ 1.58 (s, 6H), 1.62 (s, 3H), 1.66 (s, 3H), 1.84 (m, 2H), 1.90-2.10 (m, 8H), 2.22 (q, J=7.2 Hz, 2H), 2.32 (s, 6H), 3.80 (t, J=6.5 Hz, 2H), 5.08 (m, 2H), 5.14 (m, 1H), 7.89 (s, 2H);MS m/e 400 (MH+). Anal. calcd. for $C_{25}H_{37}N_1O_3$: C, 75.15; H, 9.33; N, 3.51. Found: C, 75.59; H, 9.45; N, 3.46.

The nitro aromatic compound (10.7 g, 0.027 mmole) and stannous chloride (33.8 g, 0.15 mole) were dissolved in 150 mL of absolute ethanol and heated to about 70° for about 30 minutes. The mixture was poured into water and the pH was adjusted to 7.0 with 30% NaOH causing a heavy white precipitate. The tin salts were removed by filtration (celite) and the resulting material was extracted with ether. The ether extracts were dried (brine, $MgSO_4$) and concentrated to an oil which was purified by flash chromatography (gradient 9:1 to 4:1 hexane: ether) to yield the compound of the present Example (5.92 g, mmole, 59%) as a yellow oil. The sample was further purified by distillation in a Kugelrohr oven (bath 160°-170°/0.05 mm) to yield a pale yellow oil: IR (film) 3450, 3364, 2922, 1620, 1488, 1380, 1216, 846 cm⁻¹; ¹H NMR (CDCl₃) δ 1.59 (s, 6H), 1.61 (s, 3H), 1.66 (s, 3H), 1.80 (m, 2H), 1.90-2.10 (m, 8H), 2.15 (m, 2H), 2.17 (s, 6H), 3.38 (br s, 2H), 3.67 (t, J=6.4 Hz, 2H), 5.08 (m, 2H), 5.16 (m, 1H), 6.33 (s, 2H); MS m/e 369 (M+). Anal. calcd. for $C_{25}H_{39}N_1O_1$: C, 81.25; H, 10.64; N, 3.79. Found: C, 81.30; H, 10.81; N, 3.76.

EXAMPLE 27

N-[[3,5-Dimethyl-4-[(5,9,13-Trimethyl-4(E), 8(E), 12-tetradecatrienyl)oxy]]phenyl]methyl carbamate

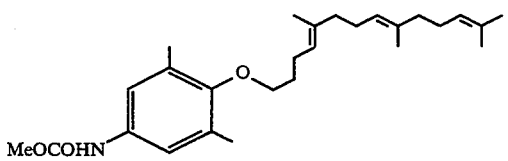

The compound of the present Example was prepared in the same manner (from compound of Example 26) as the compound of Example 25 using methyl chloroformate as the acylating agent. The compound of the present Example (42%) was isolated as a light brown oil: IR (film) 3322, 2924, 1738, 1712, 1612, 1544, 1440, 1216, 1164 cm⁻¹; ¹H NMR (CDCl₃) δ 1.58 (s, 6H), 1.61 (s, 3H), 1.66 (s, 3H), 1.81 (m, 2H), 1.90-2.10 (m, 8H), 2.16 (m, 2H), 2.22 (s, 6H), 3.70 (t, J=6.4 Hz, 1H), 3.73 (s, 3H), 5.08 (m, 2H), 6.39 (br s, 1H), 6.99 (s, 1H); MS m/e 427 (M+). Anal. calcd. for $C_{27}H_{41}N_1O_3$: C, 75.84; H, 9.66; N, 3.28. Found: C, 75.84; H, 9.60; N, 3.20.

EXAMPLE 28

4-[(5,9,13-Trimethyl-4(E), 8(E),12-Tetradecatrienyl)oxy]benzenesulfonamide

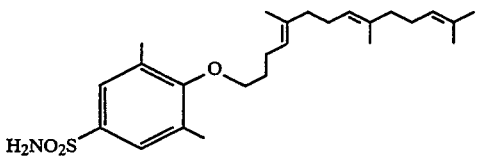

The compound of the present example was prepared from 4-hydroxybenzenesulfonamide using the procedure described in Example 4. The product was isolated as an off white waxy solid (43%), mp>60°: IR (film) 3362, 3266, 2926, 1598, 1334, 1316, 1262, 1158 cm⁻¹; ¹H NMR (CDCl₃) δ 1.57 (s, 9H), 1.65 (s, 3H), 1.84 (m, 2H), 1.90-2.10 (m, 8H), 2.15 (m, 2H), 3.97 (t, J=6.4 Hz, 2H), 4.73 (br s, 2H), 5.08 (m, 2H), 5.12 (m, 1H), 6.94 (d, J=8.9 Hz, 2H), 7.82 (d, J=8.9 Hz, 2H); MS m/e 460 (MH+). Anal. calcd. for $C_{23}H_{35}N_1O_3S_1$: C, 68.11; H, 8.70; N, 3.45. Found: C, 68.25; H, 8.76; N, 3.44.

EXAMPLE 29

2,4,6-Tris-[4-[(5,9,13-Trimethyl-4(E), 8(E),12-tetradecatrienyl)oxy]phenyl]boroxin

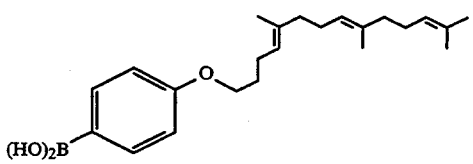

n-Butyllithum (2.7 mL, 2.5M) was added dropwise to a solution of 1-bromo-4-[(5,9,13-trimethyl-4(E), 8(E),12-tetradecatrienyl)oxy]benzene [prepared as indicated in Example 4, colorless oil (66%)] [Kugelrohr oven (bath 145°–155°/0.15 mm)]: IR (film) 2924, 1592, 1578, 1490, 1470, 1448, 1286, 1244, 1170, 822 cm-1; 1H NMR (CDCl3) 1.55 (s, 9H), 1.66 (s, 3H), 1.79 (m, 2H), 1.90–2.10 (m, 8H), 2.14 (q,J=7.2 Hz, 2H), 3.88 (t, J=6.4 Hz, 2H), 5.07 (m, 2H), 5.12 (m, 1H), 6.74 (d, J=8.8 Hz, 2H), 7.33 (d, J=8.8 Hz, 2H); MS m/e 405, 407 (MH+). Anal. calcd. for $C_{23}H_{33}BrO_1$: C, 68.14; H, 8.20. Found: C, 68.47; H, 8.12] (2.6 g, 6.43 mmole) in 20 mL of dry THF at −78°, under $N_2$. After about 30 minutes at about −78°, triisopropyl borate (16 mL, 7.08 mmole) was added to the mixture and the solution was warmed to about 10°. After stirring for about 2 hours at about 10°, the mixture was poured into 1N HCl and extracted with ether. The organic layers were dried (brine, $MgSO_4$) and concentrated in vacuo to a colorless oil. The crude material was purified by flash chromatography (gradient 5:1 to 2:1 hexanes: ether) to yield 1.4 g (3.78 mmole, 59%) of a thick, colorless oil which dehydrated upon drying, to give the cyclic anhydride (compound of present Example) as a thick colorless oil: IR (film) 2924, 1604, 1412, 1346, 1306, 1246, 1172 cm-1; 1H NMR (CDCl3) δ 1.58 (s, 6H), 1.59 (s, 3H), 1.66 (s, 3H), 1.85 (m, 2H), 1.90–2.10 (m, 8H), 2.18 (m, 2H), 4.02 (t, J=6.3 Hz, 2H), 5.08 (m, 2H), 5.16 (m, 1H), 6.98 (d, J=8.3 Hz, 2H), 8.13 (d, J=8.3 Hz, 2H); MS m/e 438 (FAB/Diethanolamine Matrix). Anal. calcd. for $C_{69}H_{99}B_3O_6$: C, 78.41; H, 9.45. Found: C, 78.22; H, 9.37.

EXAMPLE 30

4-[(5,9,13-Trimethyl-4(E), 8(E),12-tetradecatrienyl) thio]phenol

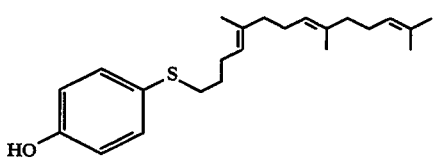

The compound of the present Example was prepared from 4-hydroxythiophenol using the procedure described in Example 3. The product was isolated as a colorless oil (76%) [Kugelrohr oven (bath 180°–190°/0.07 mm)]: IR (film) 3400, 2930, 1600, 1585, 1495, 1440, 830 cm-1; 1H NMR (CDCl3) δ 1.57 (s, 9H), 1.61 (m, 2H), 1.65 (s, 3H), 1.90–2.10 (m, 10H), 2.77 (t, J=7.2 Hz, 2H), 4.88 (s, 1H), 5.07 (m, 3H), 6.74 (d, J=8.7 Hz, 2H), 7.26 (d, J=8.7 Hz, 2H); MS m/e 359 (MH+). Anal. calcd. for $C_{23}H_{34}O_1S_1$, 0.2 H2O: C, 76.28; H, 9.59; H2O, 1.0. Found: C, 76.39; H, 9.56; H2O, 2.47.

EXAMPLE 31

4-[(5,9,13-trimethyl-4(E),8(E),12-tetradecatrienyl) sulfinyl]phenol

The sulfide of the compound of Example 30 (1.16 g, 3.25 mmole) was dissolved in 20 mL of methanol. A solution of OXONE (6.0 g, 9.75 mmole) in water (20 mL) was added in one portion. After stirring about 15 hours at about 23° C., the mixture was poured into water and extracted into ethyl acetate. The organic layers were dried (brine, $MgSO_4$) and concentrated in vacuo. The residue was purified by flash chromatography (1:1 EtOAc: Hexane) to yield the compound of the present Example (300 mg, 0.77 mmole, 24%) as a pale yellow oil: IR (film) 3126, 2926, 1602, 1584, 1500, 1284, 1000 cm-1; 1H NMR (CDCl3) δ 1.54 (s, 6H), 1.56 (s, 3H), 1.60 (s, 3H), 1.60 (m, 2H), 1.90–2.13 (m, 10H), 2.73 (m, 1H), 2.88 (m, 1H), 5.05 (m, 3H), 6.92 (d, J=8.7 Hz, 2H), 7.42 (d, J=8.7 Hz, 2H), 8.6 (br s, 1H); MS m/e 375 (MH+). Anal. calcd. for $C_{23}H_{34}O_2S.0.5$ H2O, C, 73.80; H, 9.15. Found: C, 73.58; H, 9.17.

EXAMPLE 32

4-[(5,9,13-trimethyl-4(E),8(E),12-tetradecatrienyl)sulfonyl]phenol

The sulfide of the compound of Example 30 (1.0 g, 2.99 mmole) was dissolved in 20 mL of $CH_2Cl_2$. Tetra-n-butylammonium OXONE (3.0 g, 8.4 mmole) was added to the sulfide as a $CH_2Cl_2$ solution (30 mL). After about 30 minutes at about 23°, TLC indicated complete conversion to the sulfoxide (compound of Example 31). The mixture was heated to reflux for about 3 hours, then 3.0 g of additional TBA OXONE was added, and the mixture heated for an additional 2 hours. TLC analysis indicated complete conversion to the less polar sulfone. The mixture was cooled, diluted with ether and the precipitated solid was filtered off. The residue was purified by flash chromatography (gradient 5:1 to 1:1 hexanes: ethyl acetate) to yield the compound of the present Example (680 mg, 1.74 mmole, 62%). The oil was distilled in a Kugelrohr oven (bath 220° C./0.1 mm) to give a thick yellow oil: IR (film) 3356, 2924, 1602, 1588, 1288, 1138 cm-1; 1H NMR (CDCl3) δ 1.55 (s, 6H), 1.56 (s, 3H), 1.64 (s, 3H), 1.68 (m, 2H), 1.95–2.10 (m, 10H), 3.00 (m, 2H), 5.05 (m, 3H), 5.64 (s, 1H), 6.91 (d, J=6.8 Hz, 2H), 7.74 (d, J=6.8 Hz, 2H); MS m/e 391 (MH+). Anal. calcd. for $C_{23}H_{34}O_3S$: C, 70.73; H, 8.77. Found: C, 70.59; H, 8.82.

EXAMPLE 33

4-[6,10,14-Trimethyl-5(E), 9(E), 13-Pentadecatrienyl]phenol, p-(Methoxymethoxy) benzyl bromide [(Mylona, et al, J. Org. Chem. 1988, 53, 3838–3841) 13.79 g, 0.06 mole] and sodium p-toluenesulfinate hydrate (15 g, 0.085 mole) were dissolved in 50 ml of DMF and the mixture was stirred at about 23° for about 18 hours. The solution was diluted with water (200 ml) and the white solid was filtered and washed with water. Recrystallization from ethyl acetate/hexanes provided the sulfone (FIG. 3) (13.7 g, 0.045 mole, 75%) as white needles, mp 102°–103°: IR (KBr) 2954, 1610, 1512, 1310, 1300, 1290, 1246 cm-1; 1H NMR (CDCl3) δ 2.41 (s, 3H), 3.45 (s, 3H), 4.22 (s, 2H), 5.14 (s, 2H), 6.91 (d, J=8.8 Hz, 2H), 6.99 (d, J=8.8 Hz, 2H), 7.24 (d, J=8.0 Hz, 2H), 7.52 (d, J=8.0 Hz, 2H); MS m/e 307 (MH+). Anal. calcd. for C$_{16}$H$_{18}$O$_4$S$_1$: C, 62.73; H, 5.93. Found: C, 62.71; H, 5.90.

The sulfone (FIG. 3) (5.0 g, 16.3 mmole) was dissolved in 30 mL of dry THF/6 mL of dry HMPA. The mixture was cooled to −78° under N$_2$, then n-butyllithium (6.4 mL, 17.1 mmole, 2.5M hexanes) was added, giving rise to a pale orange anion. After stirring at about −78° for about 3 hours, farnesylethyl iodide (6.43 g, 17.9 mmole) was added dropwise as a THF solution (5 mL). The mixture was stirred at about −78° for about 1.5 hours then at about 23° for about 0.5 hour then poured into water. The product was extracted into ether and the organic layers were dried (brine, MgSO$_4$) and concentrated in vacuo. Purification by flash chromatography (6:1 hexanes: ether) yielded the alkylated sulfone (FIG. 3) (6.44 g, 12 mmole, 75%) as a colorless oil: IR (film) 2924, 1610, 1512, 1316, 1302, 1238, 1146 cm$^{-1}$; $^1$H NMR (CDCl$_3$) δ 1.22 (m, 2H), 1.55 (s, 3H), 1.58 (s, 3H), 1.60 (s, 3H), 1.68 (s, 3H), 1.93–2.04 (m, 10H), 2.30 (m, 2H), 2.40 (s, 3H), 3.48 (s, 3H), 3.95, 3.99 (d of d, J=11.75, 3.50 Hz, 1H), 5.00 (m, 1H), 5.09 (m, 2H), 5.16 (s, 2H), 6.91 (d, J=8.75 Hz, 2H), 7.03 (d, J=8.75 Hz, 2H), 7.19 (d, J=8.2 Hz, 2H), 7.42 (d, J=8.2 Hz, 2H); MS m/e 538 (M+). Anal. calcd. for C$_{33}$H$_{46}$O$_4$S$_1$: C, 73.57; H, 8.61. Found: C, 73.58; H, 8.36.

Sulfone (FIG. 3) (5.97 g, 0.011 mole) was dissolved in 50 mL of dry methanol. Disodium hydrogen phosphate (6.33 g, 0.045 mole) was added to the cooled (5°) methanol mixture followed by 6% sodium amalgam (16.7 g). The mixture was stirred at about 5° for about 15 minutes then at about 23° for about 2 hours. The solution was decanted into water from the mercury and the aqueous solution was acidified to pH 5 with 10% HCl. The product was extracted into ether and the organic layers were dried (brine, MgSO$_4$) and concentrated in vacuo. The crude material was purified by flash chromatography (5:1 hexanes: ether) and Kugelrohr distillation (bath 145°–150°/0.1 mm) to yield the methoxymethoxy ether (FIG. 3) (3.84 g, 10.0 mmole, 91%) as a pale yellow oil: IR (film) 2926, 1612, 1512, 1442, 1232, 1154, 1012 cm$^{-1}$; $^1$H NMR (CDCl$_3$) δ 1.35 (m, 2H), 1.58 (s, 9H), 1.67 (s, 3H), 1.93–2.10 (m, 10H), 2.53 (t, J=7.6 Hz, 2H), 3.46 (s, 3H), 5.08 (m, 3H), 5.14 (s, 2H), 6.91 (d, J=8.6 Hz, 2H), 7.07 (d, J=8.6 Hz, 2H); MS m/e 385 (MH+). Anal. calcd. for C$_{26}$H$_{40}$O$_2$: C, 81.20; H, 10.48. Found: C, 81.29; H, 10.37.

The mom-ether (FIG. 3) (3.07 g, 7.99 mmole) and p-toluenesulfonic acid (350 mg, 1.8 mmole) were dissolved in 100 mL of methanol under N$_2$. The mixture was heated to reflux for about 1 hour then poured into water. The product was extracted into ether and the organic layers were washed (NaHCO$_3$ soln.), dried (brine, MgSO$_4$) and concentrated in vacuo. The crude material was purified by flash chromatography (6:1 hexanes: ether) and Kugelrohr distillation (bath 165°–175°/oil mm) to yield the compound of the present Example (2.4 g, 7.07 mmole, 88%) as a pale yellow oil: IR (film) 3354, 2926, 1614, 1514, 1234, 828 cm$^{-1}$; $^1$H NMR (CDCl$_3$) δ 1.34 (m, 2H), 1.58 (s, 9H), 1.66 (s, 3H), 1.93–2.10 (m, 10H), 2.51 (t, J=7.5 Hz, 2H), 4.63 (s, 1H), 5.08 (m, 3H), 6.72 (d, J=8.4 Hz, 2H), 7.02 (d, J=8.4 Hz, 2H); MS m/e 341 (MH+). Anal. calcd. for C$_{24}$H$_{36}$O$_1$: C, 84.65; H, 10.66. Found: C, 84.45; H, 10.67.

EXAMPLE 34

4-[2-(5,9,13)-Trimethyl-4(E), 8(E), 12-tetradecatrienyl)-1,3-dithian-2-yl]phenol

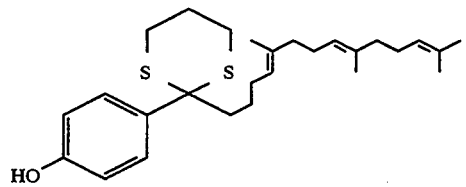

The compound of the present Example was obtained from the silyl ether (FIG. 2) (as prepared in Example 35) using the same procedure as that described for the compound of Example 12. The purified compound was isolated as a pale yellow oil: IR (film) 3398, 2930, 1608, 1504, 1432, 1172 cm$^{-1}$; $^1$H NMR (CDCl$_3$) δ 1.25 (m, 2H), 1.50 (s, 3H), 1.54 (s, 3H), 1.57 (s, 3H), 1.64 (s, 3H), 1.80–2.10 (m, 14H), 2.64 (m, 4H), 4.81 (s, 1H), 4.96 (m, 1H), 5.Q5 (m, 2H), 6.79 (d, J=8.9 Hz, 2H), 7.72 (d, J=8.9 Hz, 2H); MS m/e 445 (MH+). Anal. calcd for C$_{27}$H$_{40}$O$_1$S$_1$: C, 72.92; H, 9.07. Found: C, 72.56; H, 9.42.

EXAMPLE 35

1-(4-Hydroxyphenyl)-6,10,14-Trimethyl-5(E), 9(E), 13-Pentadecatrien-1- One

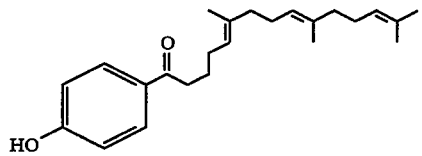

4-(1,3-Dithian-2-Yl)phenol (5.0g, 23.7 mmole) (Fernandez et al, *Eur. J. Med. Chem. Chim. Ther.*, 19: 461–464 (1984)) imidazole (3.2 g, 47.4 mmole) and t-butyldimethylsilyl chloride (3.8 g, 24.9 mmole) were dissolved in 10 mL of dry DMF and stirred at about 23° for about 18 hours. The mixture was poured into water, extracted into ether and-the organic layers were dried (brine, MgSO$_4$) and concentrated in vacuo. The crude material was purified by flash chromatography (30:1 hexanes: ether) to give the silyl ether (FIG. 2) (4.9 g, 15.3 mmole, 63%) as a white solid, mp 85°–87°: IR (KBr) 2926, 1506, 1254, 908 cm$^{-1}$; $^1$H NMR (CDCl$_3$) δ 0.16 (s, 6H), 0.94 (s, 9H), 1.90 (m, 1H), 2.14 (m, 1H), 2.87 (m, 2H), 3.04 (m, 2H), 5.10 (s, 1H), 6.76 (d, J=8.6 Hz, 2H), 7.30 (d, J=8.6 Hz, 2H); MS m/e 327 (MH+). Anal. calcd. for C$_{16}$H$_{26}$O$_1$S$_2$Si$_1$: C, 58.84; H, 8.02. Found: C, 58.96; H, 8.38.

The silyl ether (FIG. 2) (1.8 g, 5.56 mmole) was dissolved in 10 mL of dry THF and the solution was cooled to about −78° under nitrogen. n-Butyllithium (2.3 mL, 2.5M in hexanes, 5.83 mmole) was added dropwise and the mixture was stirred for 1 hour at about −78°, taken to 0°, then chilled back to about −78°. A solution of farnesylethyl iodide (2.0 g, 5.56 mmole) in THF (3 mL) was added to the metalated dithiane. After about 2 hours at about −78° the mixture was warmed to about 10° and quenched with saturated NH$_4$Cl solution. The solution was poured into water, extracted into ether, and the organic extracts were dried (brine, MgSO$_4$) and concentrated in vacuo. The crude material was chromatographed (100:1 hexanes: ether) to yield the t-butyldimethylsilyl ether (FIG. 2) (2.5 g, 4.48 mmole, 81%) as a thick colorless oil: IR (film) 2930, 1500, 1264, 918 cm$^{-1}$; $^1$H NMR (CDCl$_3$) δ 0.19 (s, 6H), 0.96 (s, 9H), 1.25 (m, 2H), 1.49 (s, 3H), 1.55 (s, 3H), 1.57 (s, 3H) 1.65 (s, 3H), 1.80–2.10 (m, 14H), 2.65 (m, 4H), 4.96 (m, 1H), 5.08 (m, 2H), 6.79 (d, J=8.7 Hz, 2H), 7.69 (d, J=8.7 Hz, 2H); MS m/d 559 (MH+). Anal. calcd. for C$_{33}$H$_{54}$O$_1$S$_2$Si$_1$: C, 70.91; H, 9.74. Found: C, 70.96; H, 9.84.

The dithiane and silyl ether were simultaneously removed from the alkylated compound (FIG. 2) (600 mg, 1.08 mmole) by treatment with mercuric acetate (688 mg, 2.16 mmole) in wet ethanol (10 mL) after stirring at about 23° for about 18 hours. The compound of the present Example (230 mg, 0.65 mmole, 60%) was isolated after flash chromatography (10:1 hexanes: ether) as a colorless oil: IR (film) 3294, 2926, 1602, 1580, 1238, 1168 cm$^{-1}$; $^1$H NMR (CDCl$_3$) δ 1.56 (s, 9H), 1.65 (s, 3H), 1.70–1.80 (m, 2H), 1.90–2.10 (m, 10H), 2.89 (t, J=7.4 Hz, 2H), 5.09 (m, 3H), 6.24 (br s, 1H), 6.87 (d, J=6.8 Hz, 2H), 7.88 (d, J=6.8 Hz, 2H); MS m/e 355 (MH+). Anal. calcd for C$_{24}$H$_{34}$O$_2$: C, 81.31; H, 9.67. Found: C, 81.06; H, 9.89.

EXAMPLE 36

4-[(5,9,13-Trimethyl-4(E), 8(E),12-tetradecatrienyl)amino]phenol

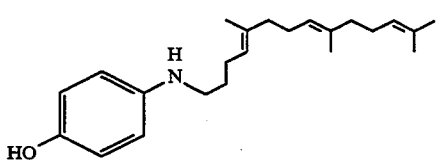

4-Aminophenol (220 mg, 2.0 mmole) and E,E-farnesylacetaldehyde (Mikani, et al, J. Org. Chem., 46: 5447–5449 (1981)) (500 mg, 2.0 mmole) were heated to reflux in benzene under azeotropic removal of water. After about 5 hours the benzene was removed in vacuo and the residue was dissolved in methanol. Sodium borohydride (80 mg, 2.1 mmole) was added portionwise to the methanol solution and the mixture was stirred for about 2 hours at about 23°. The solution was poured into water and extracted with ether. The ether extracts were dried (brine, MgSO$_4$) and concentrated in vacuo to give a crude residue which was purified by flash chromatography (gradient 10:1–10:2 hexanes: ether). The major fraction appeared by NMR to be a bis-alkylation product. The more polar minor fraction (100 mg, 0.29 mmole, 15%) was consistent with the monoalkylation adduct (compound of the present Example), and was isolated as a brown oil: IR (film) 3320, 2924, 1514, 1440, 1234, 820 cm$^{-1}$; $^1$H NMR (CDCl$_3$) δ 1.58 (s, 9H), 1.59 (m, 2H), 1.66 (s, 3H), 1.90–2.10 (m, 10H), 3.04 (t, J=7.0 Hz, 2H), 5.07 (m, 2H), 5.13 (m, 1H), 5.50 (d, J=6.6 Hz, 2H), 5.68 (d, J=6.6 Hz, 2H); MS m/e 342 (MH+). Exact Mass Calcd. for 342.2796. Found: 342.2800.

EXAMPLE 37

1,1-Dimethylethyl-(4-Hydroxyphenyl)-(5,9,13-Trimethyl-4(E), 8(E),12-tetradecatrienyl) carbamate

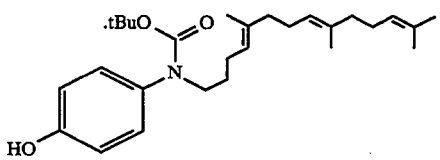

t-Butyl-(4-t-butylsilyloxyphenyl) carbamate (900 mg, 2.78 mmole) was dissolved in 10 mL of dry THF. The mixture was cooled to about −78° under nitrogen and n-butyllithium (1.2 mL, 2.5M in hexanes) was added dropwise. After stirring for about 1 hour at about −78°, farnesylethyl iodide (10 g, 2 78 mmole) was added as a THF solution (3 mL). The mixture was heated to reflux for 3 days, then quenched with saturated NH$_4$Cl solution. The organic layers were chromatographed on silica gel (gradient hexanes to 20:1 hexanes: ether) to yield the silyl ether (FIG. 1) as a colorless oil (600 mg, 1.08 mmole, 39%): $^1$H NMR (CDCl$_3$) δ 0.18 (s, 6H), 0.97 (s, 9H), 1.40 (br,s, 9H), 1.56 (s, 6H), 1.59 (s, 3H), 1.60 (m, 2H), 1.66 (s, 3H), 1.90–2.10 (m, 10H), 3.54 (t, 2H), 5.08 (m, 3H), 6.76 (d, 2H), 6.98 (br d, 2H).

The silyl ether (FIG. 1 ) (1.02 g) was dissolved in 30 mL of ether and the mixture was cooled to about 5° C. while tetra-n-butyl-ammonium fluoride (2.0 mL) was added. After stirring at 5° C. for about 15 minutes, the solution was poured into water and extracted into ether, dried (brine, MgSO$_4$) and concentrated in vacuo. The compound of the present Example was isolated as a pale yellow oil (680 mg, 1.54 mmole, 84%) after flash chromatography (gradient 18:1 to 8:1 hexanes:ether): IR (film) 3354, 2928, 1698, 1664, 1516, 1450, 1408, 1158, 838 cm$^{-1}$; $^1$H NMR (CDCl$_3$) δ 1.46 (br s, 9H), 1.56 (s, 3H), 1.57 (s, 3H), 1.61 (s, 3H), 1.67 (s, 3H), 1.90–2.10 (m, 10H), 3.51 (t, 2H), 5.08 (m, 3H), 6.62 (br s, 2H), 6.93 (d, J=8.8 Hz, 2H); MS m/e 441 (M+) . Anal. calcd. for C$_{28}$H$_{43}$N$_1$O$_3$: C, 76.15; H, 9.81; N, 3.17. Found: C, 76.21; H, 10.01; N, 3.07.

EXAMPLE 38

1,1,5,9,13-Pentamethyl-4(E), 8(E), 12-tetradecatrienol

Methyllithium (14.3 mL, 1.4M ether, 20 mmole) is added dropwise to a −78° solution of farnesyl acetone (5.0 g, 19.1 mmole) in 50 mL of dry ether. The mixture is warmed to 23° and stirred an additional 3 hours. The reaction mixture is poured into water and the aqueous layer extracted with ether. The ether extracts are washed with water, dried (brine, MgSO$_4$) and concentrated. The residue is purified by flash chromatography using 20% ether in hexanes as eluant to give the alcohol 1,1,5,9,13-Pentamethyl-4(E), 8(E), 12-tretradecatrienol (4.9 g, 92%, 17.6 mmol) as a clear oil (bp 115°–125°/0.25 mmHg): IR(film) 3372, 2968, 2924, 1448, 1378, 1220, 1150, 910 cm$^{-1}$; $^1$H NMR (CDCl$_3$) δ 1.24 (s, 6H), 1.50 (m, 2H), 1.59 (s, 6H), 1.61 (s, 3H), 1.69 (s, 3H), 1.90–2.15 (m, 10H), 5.08 (m, 3H);MS 278 (M+). Anal. Calcd. for C$_{19}$H$_{34}$O$_1$: C, 81.95; H, 12.31. Found: C, 81.67; H, 12.44.

EXAMPLE 39

4-[(1,1,5,9,13-Pentamethyl-4(E), 8(E), 12-tetradecatrienyl)oxy]phenol hydrate A solution of alcohol of Example 38 (2.6 g, 9.35 mmole) in THF (3 mL) was added to a suspension of KH (1.2 g, 35% in oil, 10.3 mmole) in THF (20 mL). After stirring for about 30 minutes, copper (I) chloride (1.0 g, 10.3 mmole) was added and the mixture was stirred an additional hour. Pyridine (50 mL) and iodide 1 (4.3 g, 14.1 mmole) were added and the mixture was heated to reflux under a nitrogen atmosphere for about 15 hours. The reaction mixture is poured into 1N HCl, filtered to remove insoluble copper salts and the aqueous layer extracted with ether. The ether extracts are washed with water, dried (brine, $MgSO_4$) and concentrated. The residue is purified by flash chromatography using 1% ether in hexanes as eluant to give the ester (14 g, 33%, 3.08 mmol) as a pale yellow oil: IR(film) 2974, 2930, 1754, 1500, 1480, 1278, 1188, 902 cm$^{-1}$; $^1$H NMR (CDCl$_3$) δ 1.26 (s, 6H), 1.33 (s, 9H), 1.59 (s, 6H), 1.62 (s, 3H), 1.65 (m, 2H), 1.69 (s, 3H), 1.95–2.20 (m, 10H), 5.08 (m, 3H), 6.94 (s, 4H); MS No Parent Ion Observable. Anal. Calcd. for $C_{30}H_{46}O_3 \cdot 0.35 H_2O$: C, 78.17; H, 10.21 Found: C, 78.18; H, 9.94.

The above ester (1.3 g, 2.86 mmole) was dissolved in ether (3 mL) and added to a suspension of LAH in ether (20 mL) at 0°. The mixture was stirred for about 30 minutes then quenched with saturated $Na_2SO_4$. The reaction mixture is poured into 1N HCl, and the aqueous layer extracted with ether. The ether extracts are washed with water, dried (brine, $MgSO_4$) and concentrated. The residue is purified by flash chromatography [gradient 20:1 to 10:1 hexanes:ether] to give the phenol (10 g, 95%, 2.70 mmol) as a pale yellow oil: IR(film) 3364, 2974, 2926, 1506, 1444, 1214, 846 cm$^{-1}$; $^1$H NMR (CDCl$_3$) δ 1.23 (s, 6H), 1.59 (s, 6H), 1.62 (s, 3H), 1.65 (m, 2H), 1.69 (s, 3H), 1.95–2.20 (m, 10H), 4.47 (s, 1H), 5.08 (m, 3H), 6.70 (d, J=10.0 Hz, 2H), 6.83 (d, J=10.0 Hz, 2H); MS No Parent Ion Observable. Anal. Calcd. for $C_{25}H_{38}O_2 \cdot 0.1 H_2O$: C, 80.64; H, 10.29. Found: C, 80.47; H, 10.37.

I claim:

1. A method of treating hypercholesterolemia and hyperlipidemia which comprises administering to a patient in need of such treatment an effective amount of a method of the formula (II)

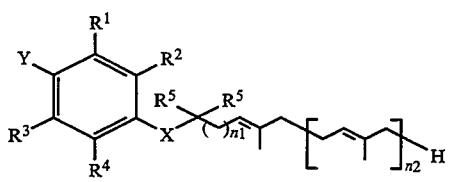

wherein $R^1$, $R^2$, $R^3$ and $R^4$ represent hydrogen, $C_1$–$C_5$ lower alkyl, halogen, $COCH_3$, $CH_2OH$, $CH_2CH_2OH$, OH or OMe;

$R^5$ represents hydrogen or methyl;

Y represents hydrogen or a hydrogen bond donating group, selected from the group consisting of $NHSO_2Me$, $NHCO_2Me$, $NH_2$, $CH_2OH$, $B(OH)_2$, $CONH_2$, $SO_2NH_2$, or OH, with the proviso that Y is not hydrogen when $R^1$, $R^2$, $R^3$ and $R^4$ are all hydrogen;

X represents oxygen, sulfur, NH, N ($C_1$–$C_5$ lower alkyl), N(acyl), $CH_2$, CO, SO, $SO_2$;

$n_1$ is 1 or 2; and $n_2$ is 1 or 2;

or nontoxic pharmaceutically acceptable acid addition salts, hydrate, solvate or metal salts thereof.

2. The method of claim 1 wherein the olefin unit in the polyprenyl side chain is all cis, all trans, or a cis/trans-mixture.

3. The method of claim 1 wherein the compound is 2,3-dimethyl-4-[5,9,13-trimethyl-4(E), 8(E), 12-tetradecatrienyl) oxy]phenol.

4. The method of claim 1 wherein the compound is 4-[(5,9,13-trimethyl-4(E), 8(E), 12-tetradecatrienyl)oxy]phenol.

5. The method of claim 1 wherein the compound is 4-[(5,9,13-trimethyl-4(E), 8(E), 12-tetradecatrienyl)thio]phenol.

6. The method of claim 1 wherein the compound is 2,3,5,6-tetrafluoro-4-[(5,9,13-trimethyl-4-(E), 8(E), 12-tetradecatrienyl) oxy]phenol.

7. The method of claim 1 wherein the compound is 1-[5-hydroxy-2-(5,9,13-trimethyl-4(E), 8(E), 12-tetradecatrienyloxy) phenyl]ethanone.

8. The method of claim 1 wherein the compound is 4-[(5,9,13-trimethyl-4(E), 8(E), 12-tetradecatrienyl)oxy]aniline.

9. The method of claim 1 wherein the compound is N-[4-(5,9,13-trimethyl-4(E), 8(E), 12-tetradecatrienyl)oxy]phenyl] methanesulfonamide.

10. The method of claim 1 wherein the compound is 4-[(5,9,13-trimethyl-4(E), 8(E), 12-tetradecatrienyl) oxy]benzenemethanol.

11. The method of claim 1 wherein the compound is 3,5-dimethyl-4-[(5,9,13-trimethyl-4(E), 8(E), 12-tetradecatrienyl) oxy]phenol.

12. The method of claim 1 wherein the compound is 2-[(5,9,13-trimethyl-4(E), 8(E), 12-tetradecatrienyl)oxy]phenol.

13. The method of claim 1 wherein the compound is 3-[(5,9,13-trimethyl-4(E), 8(E), 12-tetradecatrienyl) oxy]benzenemethanol.

14. The method of claim 1 wherein the compound is 3-[(5,9,13-trimethyl-4(E), 8(E), 12-tetradecatrienyl)oxy]phenol.

15. The method of claim 1 wherein the compound is 4-[(5,9,13-trimethyl-4(E), 8(E), 12-tetradecatrienylamino] phenol.

16. The method of claim 1 wherein the compound is 2,3-dimethyl-4-[(4,8,12-3(E), 7(E), 11-tridecatrienyl)oxy] phenol.

17. The method of claim 1 wherein the compound is 3,5-dimethyl-4-[(5,9,13-trimethyl-4(E), 8(E), 12-tetradecatrienyl) oxy]aniline.

18. The method of claim 1 wherein the compound is N-[[3,5-dimethyl-4-[(5,9,13-trimethyl-4(e), 8(E), 12-tetradecatrienyl) oxy]]phenyl]methyl carbamate.

19. The method of claim 1 wherein the compound is 2,3,5-trimethyl-4-[(5,9,13-trimethyl-4(E), 8(E), 12-tetradecatrienyl) oxy]phenol.

20. The method of claim 1 wherein the compound is 4-[(5,9,13-trimethyl-4(E), 8(E), 12-tetradecatrienyl)oxy]benzamide.

21. The method of claim 1 wherein the compound is 4-[(5,9,13-trimethyl-4(E), 8(E), 12-tetradecatrienyl)oxy] benzenesulfonamide.

22. The method of claim 1 wherein the compound is 2-hydroxy-4,6-dimethyl-5-[(5,9,13-trimethyl-4(E), 8(E), 12-tetradecatrienyl)oxy]-1,3-benzenedimethanol.

23. The method of claim 1 wherein the compound is 1-(4-hydroxyphenyl)-6,10,14-trimethyl-5(E), 9(E), 13-pentadecatrien-1-one.

24. The method of claim 1 wherein the compound is 2-hydroxy-5-[(5,9,13-trimethyl-4(E), 8(E), 12-tetradecatrienyl) oxy]benzene ethanol.

25. The method of claim 1 wherein the compound is 3,5-dimethyl-4-[(5,9,13-trimethyl-4,8,12-tetradecatrienyl)oxy]phenol.

26. The method of claim 1 wherein the compound is 3,5-dimethoxy-4-[(5,9,13-trimethyl-4(E), 8(E), 12-tetradecatrienyl) oxy]phenol.

27. The method of claim 1 wherein the compound is 4-[(1,1,5,9,13-pentamethyl-4(E), 8(E), 12-tetradecatrienyl)oxy]phenol hydrate.

28. The method of treating hypercholesterolemia according to claim 1 which comprises administering to said patient an effective amount of a compound of formula (II).

29. The method of treating hyperlipidemia according to claim 1 which comprises administering to said patient an effective amount of a compound of formula (II).

* * * * *